(12) United States Patent
Chang et al.

(10) Patent No.: US 10,094,832 B2
(45) Date of Patent: Oct. 9, 2018

(54) CERVICAL CANCER-RELATED HPV E7 PROTEIN MONOCLONAL ANTIBODY AND USE THEREOF

(71) Applicant: ATTOGEN BIOMEDICAL (SUZHOU) INC. LTD., Jiangsu (CN)

(72) Inventors: Xiaojia Chang, Jiangsu (CN); Lijun Shi, Jiangsu (CN); Chenglong Shi, Jiangsu (CN); Fengli Han, Jiangsu (CN); Yan Huang, Jiangsu (CN)

(73) Assignee: ATTOGEN BIOMEDICAL (SUZHOU) INC. LTD., Jiangsu (CN)

( * ) Notice: Subject to any disclaimer, the term of this patent is extended or adjusted under 35 U.S.C. 154(b) by 0 days.

(21) Appl. No.: 15/514,758

(22) PCT Filed: Sep. 21, 2015

(86) PCT No.: PCT/CN2015/090139
§ 371 (c)(1),
(2) Date: Jun. 23, 2017

(87) PCT Pub. No.: WO2016/045563
PCT Pub. Date: Mar. 31, 2016

(65) Prior Publication Data
US 2017/0315124 A1    Nov. 2, 2017

(30) Foreign Application Priority Data

Sep. 26, 2014  (CN) .......................... 2014 1 0503512

(51) Int. Cl.
*G01N 33/569* (2006.01)
*C07K 16/08* (2006.01)

(52) U.S. Cl.
CPC ..... *G01N 33/56983* (2013.01); *C07K 16/084* (2013.01); *C07K 2317/20* (2013.01); *C07K 2317/24* (2013.01); *C07K 2317/56* (2013.01); *C07K 2317/565* (2013.01); *C07K 2317/622* (2013.01); *G01N 2333/025* (2013.01); *G01N 2469/10* (2013.01); *G01N 2800/7028* (2013.01)

(58) Field of Classification Search
None
See application file for complete search history.

(56) References Cited

FOREIGN PATENT DOCUMENTS

| CN | 102443060 | 5/2012 |
|---|---|---|
| CN | 103254307 | 8/2013 |
| WO | 2011101122 | 8/2011 |
| WO | 2013038016 | 3/2013 |

OTHER PUBLICATIONS

International Search Report for PCT/CN2015/090139, dated Dec. 22, 2015, 11 pages including English translation.

*Primary Examiner* — Nianxiang Zou
(74) *Attorney, Agent, or Firm* — Hamre, Schumann, Mueller & Larson, P.C.

(57) ABSTRACT

The present invention provides an anti-HPV E7 protein monoclonal antibody and the use thereof. The antibody can detect the HPV16 E7 protein with high specificity and recognize the HPV18 E7 protein, thereby it can distinguish between the cancerous cervical epithelial cells and the cervical abnormal or non-cancerous cervical epithelial cells.

15 Claims, 6 Drawing Sheets

Specification includes a Sequence Listing.

|  | Sequence |
|---|---|
| FR1 | VKLQESGPELVKPGASMKISCKAS(SEQ ID NO.:11) |
| CDR1 | GYSFTGST (SEQ ID NO.:4) |
| FR2 | MNWVKQSHGKNLEWIGL(SEQ ID NO.:12) |
| CDR2 | IDPYNGVI (SEQ ID NO.:6) |
| FR3 | RYNQKFKGRATLTIDKSSSTAYMELLSLTSDDSAVYYC(SEQ ID NO.:21) |
| CDR3 | ARKLRY (SEQ ID NO.:8) |
| FR4 | WGQGTTLTVSS(SEQ ID NO.:22) |
| Heavy chain variable region | VKLQESGPELVKPGASMKISCKASGYSFTGSTMNWVKQSHGKNLEWIGLI DPYNGVIRYNQKFKGRATLTIDKSSSTAYMELLSLTSDDSAVYYCARKLRY WGQGTTLTVSS (SEQ ID NO.:10) |

Figure 3A

|  | Sequence |
|---|---|
| FR1' | ELVLTQSP SSLNVSPGEK VTMSCKSS(SEQ ID NO.:26) |
| CDR1' | QSLLNSGNQRNY (SEQ ID NO.:14) |
| FR2' | LAWYQQKPGQ PPKLLIY(SEQ ID NO.:27) |
| CDR2' | GAS (SEQ ID NO.:16) |
| FR3' | TRESGVPDRF TGSGSGTDFT LTISSVQAED LAVYYC(SEQ ID NO.:28) |
| CDR3' | QNDLSYPLT (SEQ ID NO.:18) |
| FR4' | FGAGT KLELK(SEQ ID NO.:29) |
| Light chain variable region | ELVLTQSP SSLNVSPGEK VTMSCKSSQS LLNSGNQRNY LAWYQQKPGQ PPKLLIYGAS TRESGVPDRF TGSGSGTDFT LTISSVQAED LAVYYCQNDL SYPLTFGAGT KLELK (SEQ ID NO.:20) |

Figure 3B

CERVICAL CANCER-RELATED HPV E7 PROTEIN MONOCLONAL ANTIBODY AND USE THEREOF

FIELD OF INVENTION

The present invention relates to biological detection and medicine filed and, in particular, to an anti-HPV E7 protein monoclonal antibody and use thereof.

BACKGROUND OF INVENTION

Cervical cancer is the second most common malignant tumor in female genital system. In 1949, human papilloma virus (HPV) particles were firstly discovered in wart leachate under electron microscopy by Sttauss. When Zur Hansen predicted that HPV might be the sexually transmitted carcinogenic factor in 1976, the relation between HPV infections and cervical cancers has aroused intense interest among researchers of the tumor pathogenesis. A large number of studies have convincingly proved that HPV was the main causative factor of cervical cancer, and could also cause other tumors in genital tract, mammary gland, digestive tract and respiratory tract. Recently, HPV infection rate in China has increased continuously, therefore, early prevention and treatment of cervical cancers has become extremely important.

The majority of women would be infected by genital HPV during the life time and the ratio of HPV-infected women is up to 10.4% worldwide. In most cases, HPV virus could be cleared by immune system within 1 to 2 years. However, chronic HPV infection could result in cervical intraepithelial neoplasia (CIN) such as CIN2 and CIN3, or even cervical cancer. According to previous reports, approximately 20% low-grade cervical lesions would develop into high-grade lesions and nearly 30% high-grade lesions would finally lead to malignant tumors. Therefore, early detection and prevention of HPV infection are very critical for decreasing mortality of cervical cancer and medical cost. At present, morphological test of exfoliated cervical cells by Pap smear acts as the main method for cervical cancer detection. However, the application of morphological test has been greatly limited by the high dependence on experts' experiences, difficulties in slide preparation, poor repeatability between inter-assay and intra-assay and high false-positive and false-negative rates, which usually result in low sensitivity and high rate of missed diagnosis. The positive detectable rate for early cervical cancer detection was only about 30% to 50%. In some areas, Pap smear test is replaced by liquid based cytology (LBC). LBC is a new semiautomatic or automatic technology for sample disposal, which is capable of analyzing sample automatically and providing remaining cells sample for other HPV detection. HPV DNA (e.g. HC2) detection is another wildly used molecular detection in clinic, which could assist cytological detection in identifying high-risk HPV virus. Even though HPV DNA detection is more sensitive than cell morphological detection, it still cannot distinguish continuous instantaneous infection from instantaneous infection. This is an extremely important factor for the transition of malignant tumor. Hence HPV DNA detection cannot be used to detect cancers because it is unable to reflect cancer starting (In the 2012 respective updated cervical cancers screening guidelines by America and China, exclusive use of HPV detection for screening cancers is not recommended in any age group).

HPV is a species-specific mucosa-infected virus, which belongs to small double-stranded circular DNA virus and contains about 8000 base pairs. The HPV virus contains 8 early open reading frames (E1-E8), 2 late open reading frames and one long non-coding regulatory region. In the early reading frames, E6 and E7 are the most important genes for stimulating cell growth. The study of Ziegent (2003) has confirmed that, HPV E6 and E7 genes are potential carcinogenic genes which are capable of cell transformation. The encoded E6 and E7 proteins are oncoproteins which can transform mouse epithelial cell in vitro and cause immortalization of human epithelial cell. Additionally, the persistent expression of HPV E6 and E7 proteins is necessary for maintaining immortalization in vitro. High-risk HPV E6 and E7 genes can induce cancer in nude mouse. Senung et al. (Seung H S, Jae k L, Oye S S. The relationship between cytokines and HPV-16, HPV-16E6, E7 and high-risk HPV viral load in the uterine cervix [J]. Gynecol Oncol, 2007, 104 (3):732-738) have reported that injection of HPV 16 E6 and E7 genes into mouse basal cells induces skin cancer. Therefore, the early-expression of E6 and E7 proteins of high-risk HPV is critical in carcinogenesis of cervical cancer. In carcinogenesis process, virus DNA is integrated into genome of a human cell. As control of E6 and E7 protein expression lacks, E6 and E7 are persistently expressed in epithelial cells of highly atypical cervical hyperplasia and cervical cancers. Consequently, HPV E7 protein can be a biomarker for high-grade cervical lesions and cervical cancer.

Nowadays, HPV L1 and some other auxiliary biological markers, such as $p16^{INK4A}$, Ki67 and hTERT, are mainly used in HPV clinical immunohistochemical detection. There are three reasons why there is no suitable antibody for E7 protein detection. First, the low expression quantity of HPV protein in clinical tissues and cell samples requires that an antibody of high affinity. Second, HPV virus cannot survive in laboratory under standard tissue culture technique. Third, the immunosuppression activity of E7 protein results in poor immunoreaction in an animal which is challenged with use E7 protein. Moreover, the obtained antibodies are not specific to E7 proteins, because antibodies often have cross reaction with other HPV proteins.

Therefore, it is desired in the art to provide a convenient and reliable technique for detection of cancer with infection of high-risk HPV (especially cervical cancer) which is capable of identification of HPV type in the infected cancer cells.

SUMMARY OF INVENTION

One aim of the invention is to provide an anti-HPV E7 protein monoclonal antibody and use thereof.

Another aim of the invention is to provide a method to detect HPV E7 proteins in samples and a method to identify HPV types.

Another aim of the invention is to provide an immuno-detection reagent, an immunodetection plate and a kit to detect HPV E7 proteins in samples.

The first aspect of the invention is to provide a heavy chain variable region of an antibody wherein the heavy chain variable region comprises three complementary determining regions (CDRs):
CDR1 as shown in SEQ ID NO: 4,
CDR2 as shown in SEQ ID NO: 6 and
CDR3 as shown in SEQ ID NO: 8.

In another preferred embodiment, the heavy chain variable region has the amino acid sequence as shown in SEQ ID NO: 10.

The second aspect of the invention is to provide a heavy chain of an antibody having a heavy chain variable region according to the first aspect of the present invention and a heavy chain constant region.

In another preferred embodiment, the heavy chain constant region belongs to human or mouse.

The third aspect of the invention is to provide a light chain variable region of an antibody wherein the light chain variable region comprises three complementary determining regions (CDRs):

CDR1' as shown in SEQ ID NO: 14,
CDR2' as shown in SEQ ID NO: 16 and
CDR3' as shown in SEQ ID NO: 18.

In another preferred embodiment, the light chain variable region has the amino acid sequence as shown in SEQ ID NO: 20.

The fourth aspect of the invention is to provide a light chain of an antibody having a light chain variable region according to the third aspect of the present invention and a light chain constant region.

In another preferred embodiment, the light chain constant region belongs to human or mouse.

The fifth aspect of the invention is to provide an antibody having:

(1) a heavy chain variable region according to the first aspect of the present invention; and/or
(2) a light chain variable region according to the third aspect of the present invention.

In another preferred embodiment, the antibody has a heavy chain according to the second aspect of the present invention and/or the light chain according to the fourth aspect of the present invention.

In another preferred embodiment, the antibody is an antibody specific anti-HPV. Preferably, the antibody is an antibody specific anti-HPV16 and/or anti-HPV18. Preferably, the antibody is an antibody specific anti-HPV16E7 protein and/or anti-HPV18E7 protein.

In another preferred embodiment, the antibody includes: a single chain antibody, a double chain antibody, a monoclonal antibody, a chimeric antibody (e.g. a human-mouse chimeric antibody), a murine antibody or a humanized antibody.

In another preferred embodiment, the antibody has following properties:

the affinity to HPV16 E7≤0.64 nM; and the 'HPV18 E7 protein' could be a wild type HPV18 E7 protein or a wild type HPV18 E7 derived protein. The 'HPV16 E7 protein' could be a wild type HPV16 E7 protein or a wild type HPV16 E7 derived protein.

In another preferred embodiment, the antibody has an affinity to HPV16 E7 protein≤0.64 nM and can cross-bind HPV18 E7 protein, and the binding ability of the antibody to HPV18 E7 protein is 20% to 40% of that to HPV16 E7 protein.

In another preferred embodiment, the antibody further comprises the following property:

(3) able to specifically bind with protein contains 35-39 amino acids of HPV16 E7.

In another preferred embodiment, the antibody is an IgG2b antibody.

The sixth aspect of the invention is to provide a recombinant protein having:

(i) the heavy chain variable region according to the first aspect of the present invention, the heavy chain according to the second aspect of the present invention, the light chain variable region according to the third aspect of the present invention, the light chain according to the fourth aspect of the present invention or the antibody according to the fifth aspect of the present invention, and (ii) optionally a tag sequence that assist in expression and/or purification.

In another preferred embodiment, the tag sequence comprises 6His tag.

In another preferred embodiment, the recombinant protein is specifically against HPV; preferably, specifically anti-HPV16 and/or anti-HPV18, and more preferably, specifically against HPV16 E7 protein and/or anti-HPV18 E7 protein.

The seventh aspect of the invention is to provide a polynucleotide encoding a polypeptide selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention or the antibody according to the fifth aspect of the present invention; or (2) the recombinant protein according to the sixth aspect of the present invention.

In another preferred embodiment, the polynucleotide has the sequence as shown in SEQ ID NO: 3, 5, 7, 9, 13, 15, 17 or 19.

The eighth aspect of the invention is to provide a carrier comprising the polynucleotide according to the seventh aspect of the present invention.

In another preferred embodiment, the carrier includes bacterial plasmids, phages, yeast plasmids, plant cell virus and mammalian cell virus, for instance adenovirus, retrovirus or other carriers.

The ninth aspect of the invention is to provide a genetically engineered host cell comprising the carrier according to the eighth aspect of the present invention or in which a polynucleotide according to the seventh aspect of the invention is integrated in its chromosome.

The tenth aspect of the invention is to provide an immunoconjugate comprising:

(a) the heavy chain variable region according to the first aspect of the present invention, the heavy chain according to the second aspect of the present invention, the light chain variable region according to the third aspect of the present invention, the light chain according to the fourth aspect of the present invention or the antibody according to the fifth aspect of the present invention;

(b) a coupling moiety selected from the group consisting of a detectable label, a drug, a toxin, a cytokine, a radionuclide, or an enzyme.

In another preferred embodiment, the coupling moiety is selected from the group consisting of a fluorescent or luminescent label, a radiolabel, a MRI (magnetic resonance imaging) or CT (computed X-ray tomography) contrast agent, or an enzyme capable of producing detectable products, a radionuclide, a biotoxin, a cytokine (e.g., IL-2, etc.), an antibody, an antibody Fc fragment, a scFv antibody fragment, a gold nanoparticle/nanorod, a virus particle, a liposome, a nano-magnetic particle, a prodrug activating enzyme (e.g., DT-diaphorase (DTD) or a biphenyl hydrolase-like protein (BPHL)), a chemotherapeutic agent (e.g., cisplatin) or a nano-particle in any form.

The eleventh aspect of the invention is to provide a pharmaceutical composition comprising:

(i) the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, or the immunoconjugate according to the tenth aspect of the present invention;

(ii) a pharmaceutically acceptable carrier.

In another preferred embodiment, the pharmaceutical composition is in the form of an injection.

In another preferred embodiment, the pharmaceutical composition is used for preparing a medicament for treating a tumor selected from the group consisting of gastric cancer, liver cancer, leukemia, kidney cancer, lung cancer, small bowel cancer, bone cancer, prostate cancer, colorectal cancer, breast cancer, colon cancer, prostate cancer, cervical cancer, adrenal tumor, or bladder tumor.

The twelfth aspect of the invention is to provide a use of the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, or the immunoconjugate according to the tenth aspect of the present invention for preparing an agent, a reagent, a detection plate or a kit;

wherein the reagent, the detection plate or the kit is used for:

(1) detecting a HPV E7 protein in a sample; and/or (2) detecting endogenous HPV E7 protein in tumor cells; and/or (3) detecting tumor cells expressing the HPV E7 protein; and/or (4) identifying the type of HPV E7 protein;

the agent is used for the treatment or prevention of tumors expressing HPV E7 proteins.

In another preferred embodiment, the HPV E7 protein includes HPV16 E7 protein and/or HPV18 E7 protein.

In another preferred embodiment, the samples contain HPV18 E7 protein and HPV16 E7 protein.

In another preferred embodiment, the tumors include the tumors of urogenital system, small cell lung cancer, melanoma or head and neck cancer, gastric cancer, liver cancer, leukemia, kidney cancer, lung cancer, small bowel cancer, bone cancer, prostate cancer, colorectal cancer, breast cancer, colon cancer, prostate cancer, or adrenal tumors.

In another preferred embodiment, the tumors of urogenital system include cervical cancers, bladder cancers, endometrial cancers or penile cancers.

In another preferred embodiment, the reagents include chips, antibody-coated immune-particles.

The thirteenth aspect of the invention is to provide a method to detect a HPV E7 protein in a sample, wherein the method comprises the steps of:

(1) contacting a sample with the antibody according to the fifth aspect of the invention;

(2) detecting whether an antigen-antibody complex is formed, wherein the formation of the complex indicates the presence of a HPV E7 protein in the sample. In another preferred embodiment, ELISA is used for detection in step (2).

In another preferred embodiment, the HPV E7 protein includes HPV16 E7 protein and/or HPV18 E7 protein.

In another preferred embodiment, in step (1), the sample is contacted with two antibodies against the HPV E7 protein and then ELISA is used for detection in step (2), wherein at least one of the two antibodies is the antibody according to the fifth aspect of the present invention.

In another preferred embodiment, the antigen-antibody complex is a ternary complex of 'first antibody-antigen-second antibody', wherein the first antibody is the antibody according to the fifth aspect of the present invention and the binding epitope of the second antibody is different from that of the first antibody.

In another preferred embodiment, the second antibody is the monoclonal antibody produced by hybridoma cell lines CGMCC NO. 5200.

In another preferred embodiment, the antigen-antibody complex is a ternary complex of 'first antibody-antigen-second antibody', wherein the first antibody is the antibody according to the fifth aspect of the present invention and the binding epitope of the second antibody is different from that of the first antibody.

In another preferred embodiment, in step (1), after the sample is contacted with the antibody according to the fifth aspect of the present invention, a third antibody against the first antibody is further added to the reaction system, and the formation of the "antigen-first antibody-third antibody" complex is detected in step (2).

In another preferred embodiment, the first antibody, second antibody or third antibody are marked with detectable labeling.

In another preferred embodiment, the detectable labeling is biotin labeling, colloidal gold labeling, horseradish peroxidase labeling, radionuclide labeling and fluorescence labeling.

In another preferred embodiment, the sample includes tissue samples from human or animal, resected tumor samples, cast-off cell samples.

In another preferred embodiment, the method is used for non-diagnostic purposes.

In another preferred embodiment, the method further comprises step (3), analysis of the affinities of the antibody and the antigen. According to the analysis, the type of HPV could be identified. Many conventional methods could be used to conduct the step of 'analysis of the affinity of antibody and antigen'. For example, referring to the method raised by Beatty et al. (J. David Beatty, Barbara G. Beatty and William G. Vlahos 1987), the affinity can be analyzed and the results can be compared with reference for identifying infection type of HPV. The reference is reaction between the antibody and a standard HPV18 E7 protein and HPV16 E7 protein respectively. Additionally, the method of cell staining is also acceptable, the antibody are used to conduct reactions with the sample, cancer cells expressing HPV18 E7 protein and cancer cells expressing HPV16 E7 protein respectively. Next is comparison of staining depth to identify infection types of HPV.

The fourteenth aspect of the invention is to provide a detection plate comprising a substrate (support chip) and a test strip, wherein the test strip contain the antibody according to the fifth aspect of the present invention or the immunoconjugate according to the tenth aspect of the present invention.

In another preferred embodiment, the test strip further contains an antigen sampling area.

In another preferred embodiment, the test strip is composed of filter paper, chromatography material, nitrocellulose filter and absorbent paper orderly.

The fifteenth aspect of the invention is to provide a reagent kit comprising:

(1) the first container comprising the antibody according to the fifth aspect of the present invention; and/or (2) the second container comprising the second antibody anti the antibody according to the fifth aspect of the present invention; and/or (3) the third container comprising reagents for cell lysis; or the reagent kit comprises the detection plate according to the fourteenth aspect of the present invention.

In another preferred embodiment, the antibody in the first container is tagged with detectable labeling.

In another preferred embodiment, the antibody in the second container is tagged with detectable labeling.

The sixteenth aspect of the invention is to provide a preparation method of a recombinant polypeptide comprising following steps:

(a) culturing the host cell according to the ninth aspect of the invention under conditions suitable for expression;

(b) isolating the recombinant polypeptide from the culture, wherein the recombinant polypeptide is the antibody according to the fifth aspect of the present invention or the recombinant protein according to the sixth aspect of the present invention.

It should be understood that, within the scope of the present invention, the technical features specifically described above and below (such as in the Examples) can be combined with each other, thereby constituting a new or preferred technical solution which needs not be described one by one.

DESCRIPTION OF THE DRAWINGS

FIG. 2A shows amino acid sequence of HPV16 E7 and FIG. 2B shows the ELISA results. 7B6 is able to combine with recombinant proteins His-HPV16 E7, His-HPV1618 and polypeptide His-HPV16 E7-2, but cannot combine with polypeptide HPV16 E7-1 and HPV18 E7.

FIG. 3 shows the CDRs gene sequences of VH and VL of 7B6 monoclonal antibody immunoglobulin. Experimental details are in Example 1, Section 2.4: FIG. 3A shows the CDR gene sequences of VH of 7B6 monoclonal antibody and FIG. 3B shows the CDR gene sequences of VL of 7B6 monoclonal antibody.

DETAILED DESCRIPTION OF THE INVENTION

Figure 1:
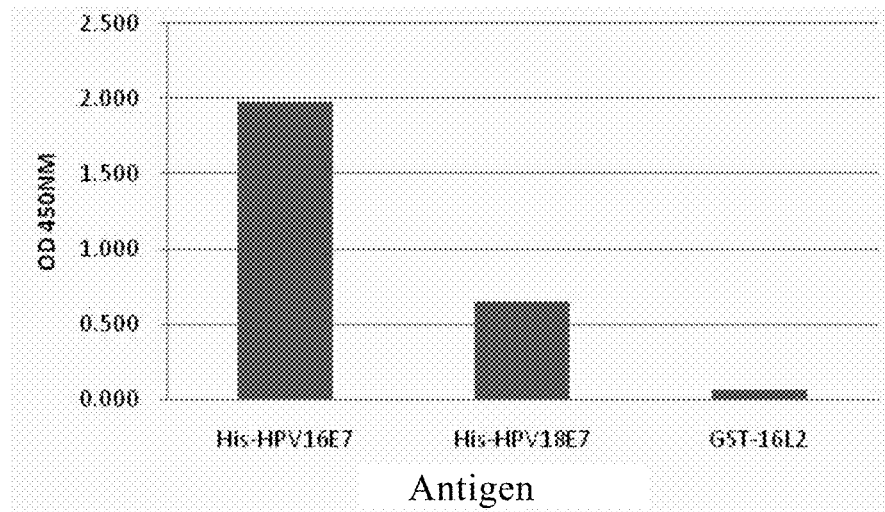
FIG. 1 shows the result of ELISA analysis of antigen specificity of HPV16 E7 monoclonal antibody 7B6. Experimental details are in Example 1, Section 2.2: the ELISA results showing that 7B6 can combine with recombinant proteins HPV16 E7 and HPV18 E7, but no combination between 7B6 with another recombinant protein HPV16 L2. Therefore, 7B6 is able to recognize the same part of peptide epitopes of HPV16 E7 and HPV18 E7.

Through extensive and intensive researches and after a large number of screening, the inventors have unexpectedly discovered an anti-HPV16 E7 monoclonal antibodies 7B6. The results showed that the monoclonal antibody of HPV E7 proteins has high-specificity and strong-affinity. It can significantly distinguish HPV E7 proteins in cells, especially for HPV16 E7 proteins. The monoclonal antibody can combine with HPV16 E7 proteins and HPV18 E7 proteins respectively with significantly different binding activities. Therefore, the monoclonal antibody can not only be used to detect HPV E7 proteins (including HPV16 E7 proteins and HPV18 E7 proteins), but also identify different types of HPV. The invention also provides a method to detect and/or identify HPV E7 proteins which has good stability and high detection sensitivity. The invention also provides reagent kits and detection plates comprising the above antibody.

Specifically, the invention uses a immune-recombinant GST-HPV16 E7 fusion protein to immunize mice and uses another fusion protein His-HPV16 E7 as a detection antigen for screening. All selected positive clonal hybridoma cells are able to secrete antibody IgG and are able to bind to His-HPV16 E7 recombinant proteins and specifically bind to HPV E7 fusion proteins in ELISA.

In addition to the identification using ELISA detection with recombinant protein antigen, positive monoclonal antibodies were further subjected to antigen-binding epitope analysis, affinity binding characterization, western blot, immunoprecipitation, immunocytochemistry ICC and immunohistochemistry IHC. The results of the above assays indicate that the antibody clone 7B6 can specifically combine with high risk HPV E7 oncoprotein in protein molecular level, cell level and tissue level.

In order to screen clinically valued antibody reagents, the monoclonal antibody was further tested by detection for cervical cancer cell lines. Eventually, a monoclonal antibody which can specifically identify HPV-positive cervical epithelial cells was obtained. And a method for distinguishing cervical epithelial cancer cells and normal cells based on the specificity of the antibody was developed, which was sufficient to identify those early cervical Cancer patients, and specific enough to distinguish normal and malignant tumor cells.

In a preferred embodiment of the invention, the amino acid sequence of the HPV16 E7 protein is:

(SEQ ID NO.: 1)
HGDTPTLHEYMLDLQPETTDLYCYEQLNDSSEEEDEIDGPAGQAEPDRA

HYNIVTFCCKCDSTLRLCVQSTHVDIRTLEDLLMGTLGIVCPICSQKP.

In a preferred embodiment of the invention, the amino acid sequence of the HPV18 E7 protein is:

(SEQ ID NO.: 2)
MHGPKATLQDIVLHLEPQNEIPVDLLCHEQLSDSEEENDEIDGVNHQHL

PARRAEPQRHTMLCMCCKCEARIELVVESSADDLRAFQQLFLNTLSFVC

PWCASQQ.

The term "antibody" or "immunoglobulin" as used herein refers to a heterotetrameric glycoprotein having the same structural feature of about 150,000 daltons consisting of two identical light chains (L) and two identical heavy chains (H). Each light chain is linked to a heavy chain by a covalent disulfide bond, and the numbers of disulfide bonds between the heavy chains of different immunoglobulin isoforms are different. Each heavy and light chain also has regularly spaced intrachain disulfide bonds. One end of each heavy chain has a variable region (VH) followed by a plurality of constant regions. There is a variable region (VL) at one end of each chain and a constant region at the other end; the constant region of the light chain corresponds to the first constant region of the heavy chain; the variable region of the light chain corresponds to the variable region of the heavy chain. There is an interface formed between the variable regions of the light and heavy chains by particular amino acid residues.

As used herein, the term "variable" means that some certain portions of the variable region of an antibody differ in sequence and contribute to the binding and specificity of each particular antibody to its particular antigen. However, the variability is not evenly distributed throughout the antibody variable region. It is concentrated in three regions in the light and heavy chain variable regions called complementary determining regions (CDRs) or hypervariable regions. The more conserved portions of the variable regions are referred as framework regions (FRs). The variable regions of the natural heavy and light chains each comprises four FR regions, which are in a substantially β-folded configuration, and are linked by three CDRs that form the linker ring and, in some cases, form a partial β-folded structure. The CDRs in each chain stand close together through FR regions and form the antigen-binding site of the antibody together with the CDRs of the other chain (see Kabat et al., NIH Publ. No. 91-3242, Vol. I, 647-669 (1991)). Constant regions are not directly involved in the binding of the antibodies to the antigens, but they exhibit different effector functions, such as antibody-dependent cellular cytotoxicity involved in antibodies.

The 'light chain' of vertebrate antibody (immunoglobulin) could be divided into two distinct types (κ or λ) according to the amino acid sequences of constant region. Based on the amino acid sequences of heavy chain constant region, immune globulins could be divided into different species. There are five classes of immunoglobulins: IgA, IgD, IgE, IgG and IgM, some of them could be further divided into subclass: IgG1, IgG2, IgG3, IgG4, IgA and IgA2. The heavy chain constant regions corresponding to different classes of immunoglobulins could be named as α, δ, ε, γ and μ. The subunit structures and 3D configurations of different immune globulins are well known to those skilled in the art.

As used herein, the term 'monoclonal antibody' refers to an antibody obtained from a class of substantially homogeneous population, which means the single antibody of this population is the same except for a few naturally occurring mutations. Monoclonal antibodies are highly specific to a single antigenic site. Additionally, differ from normal polyclonal antibody reagents (which possess different antibodies against different determinants normally), monoclonal antibody is specific to a single determinant. Except for their specificity, another advantage of monoclonal antibody is that they are synthesized by hybridoma culture technique and are not be polluted by other immune globulins. The modifier 'monoclonal' refers to the properties of an antibody that is obtained from a substantially homogeneous population of antibodies and it should be explained as some special methods are needed to produce the antibody.

The invention also includes the monoclonal antibody having corresponding amino acid sequences of the HPV16 E7 protein monoclonal antibody, the monoclonal antibody having the variable region chains of the HPV16 E7 protein monoclonal antibody, and other proteins or protein conjugates and fusion expression products having such chains. In particular, the present invention includes any protein or protein conjugate and a fusion expression product (i.e., an immunoconjugate and a fusion expression product) comprising a heavy chain containing a variable region as long as the variable region is identical, or at least 90% homologous, preferably at least 95% homologous, with the heavy chain variable region of the antibody of the invention.

As known to those skilled in the art, the immunoconjugates and fusion expression products include conjugates formed by drugs, toxins, cytokines, radionuclides, enzymes and other diagnostic or therapeutic molecules binding to the HPV16 E7 protein monoclonal antibody or the fragments thereof of the invention. The present invention also includes cell surface markers or antigens that bind to the anti-HPV16 E7 protein monoclonal antibodies or the fragments thereof.

The invention not only contains intact monoclonal antibody, but also includes antibody fragments with immunological activity, for instance, Fab or (Fab') 2 fragments; antibody heavy chains; antibody light chains.

As used herein, the terms "heavy chain variable region" and "VH" are used interchangeably. As used herein, the terms "variable region" and "complementary determining region (CDR)" are used interchangeably. In a preferred embodiment of the invention, the heavy chain variable region of the antibody comprises three complementary determining regions (CDRs):

CDR1: the amino acid sequence is GYSFTGST (SEQ ID NO.: 4) and the nucleotide sequence encoding CDR1 is ggttactcattcactggctccacc (SEQ ID NO.: 3);

CDR2: the amino acid sequence is IDPYNGVI (SEQ ID NO.: 6) and the nucleotide sequence encoding CDR2 is attgatccttacaatggtgttatt (SEQ ID NO.: 5);

CDR3: the amino acid sequence is ARKLRY (SEQ ID NO.: 8) and the nucleotide sequence encoding CDR3 is gcaagaaagttgcgctac (SEQ ID NO.: 7);

In a preferred embodiment of the invention, the amino acid sequence of heavy chain variable region is:

```
                                    (SEQ ID NO.: 10)
VKLQESGPELVKPGASMKISCKASGYSFTGSTMNWVKQSHGKNLEWIGL

IDPYNGVIRYNQKFKGRATLTIDKSSSTAYMELLSLTSDDSAVYYCARK

LRYWGQGTTLTVSS;
```

The nucleotide sequence encoding VH is:

```
                                    (SEQ ID NO.: 9)
GTCAAGCTGCAGGAGTCTGGACCTGAGCTGGTGAAGCCTGGAGCTTCAA

TGAAGATATCCTGCAAGGCTTCTGGTTACTCATTCACTGGCTCCACCAT

GAACTGGGTGAAGCAGAGCCATGGAAAGAACCTTGAGTGGATTGGACTT

ATTGATCCTTACAATGGTGTTATTAGGTACAACCAGAAGTTCAAGGGCA

GGGCCACATTAACTATAGACAAGTCATCCAGCACAGCCTACATGGAGCT

CCTCAGTCTGACATCTGATGACTCTGCAGTCTATTACTGTGCAAGAAAG

TTGCGCTACTGGGGCCAAGGCACCACTCTCACAGTATCCTCA.
```

In a preferred embodiment of the invention, the heavy chain of the antibody includes the heavy chain variable region and a heavy chain constant region. The sources of heavy chain constant region could be human or mice.

As used herein, the terms "light chain variable region" and "VL" are used interchangeably.

In a preferred embodiment of the invention, the light chain variable region of the antibody comprises the complementary determining regions (CDRs) selected from the group of:

CDR1': the amino acid sequence is QSLLNSGNQRNY (SEQ ID NO.: 14) and the nucleotide sequence encoding CDR1' is cagagtctgttaaacagtggaaatcaaaggaactac (SEQ ID NO.: 13);

CDR2': the amino acid sequence is GAS (SEQ ID NO.: 16) and the nucleotide sequence encoding CDR2' is ggggcatcc (SEQ ID NO.: 15);

CDR3': the amino acid sequence is QNDLSYPLT (SEQ ID NO.: 18) and the nucleotide sequence encoding CDR3' is cagaatgatcttagttatcctctcacg (SEQ ID NO.: 17);

In a preferred embodiment of the invention, the amino acid sequence of the light chain variable region is:

```
                                    (SEQ ID NO.: 20)
ATQSPSSLNVSPGEKVTMSCKSSQSLLNSGNQRNYLAWYQQKPGQPPKL

LIYGASTRESGVPDRFTGSGSGTDFTLTISSVQAEDLAVYYCQNDLSYP

LTFGAGTKLELK;
```

The nucleotide sequence encoding VL is:

```
                                    (SEQ ID NO.: 19)
GCTACACAGTCTCCATCCTCCCTGAATGTGTCACCAGGAGAGAAGGTCA

CTATGAGCTGCAAGTCCAGTCAGAGTCTGTTAAACAGTGGAAATCAAAG

GAACTACTTGGCCTGGTACCAGCAGAAACCAGGACAGCCTCCTAAACTG

TTGATCTACGGGGCATCCACTAGGGAGTCTGGGGTCCCTGATCGCTTCA

CCGGCAGTGGATCTGGAACCGATTTCACTCTTACCATCAGCAGTGTGCA

GGCTGAAGACCTGGCAGTTTATTACTGTCAGAATGATCTTAGTTATCCT

CTCACGTTCGGTGCTGGGACCAAGCTGGAGCTGAAA;
```

In a preferred embodiment of the invention, the light chain of the antibody includes the light chain variable region and a light chain constant region. The sources of described light chain constant region could be humans or mice.

In the present invention, the terms "antibody of the present invention", "protein of the present invention" or "polypeptide of the present invention" are used interchangeably and all refer to polypeptides that specifically bind to HPV16E7 protein for example, a protein or polypeptide comprising a heavy chain (e.g. SEQ ID NO.: 12 amino acid sequence) and/or a light chain (e.g. SEQ ID NO.: 22 amino acid sequence). They may or may not contain a starting methionine.

In a preferred embodiment of the invention, the antibody is a mouse or human-mouse chimeric antibody anti-HPV16 E7 proteins and their heavy chain constant region and/or light chain constant region could be humanized heavy chain constant region and/or light chain constant region. Preferably, the humanized heavy chain constant region or light chain constant region are the heavy chain constant region or light chain constant region of human, IgG1, IgG2 and etc.

The present invention also provides other proteins or fusion expression products having the antibodies of the invention. In particular, the present invention includes any protein or protein conjugate and a fusion expression product (i.e., an immunoconjugate and a fusion expression product) comprising a heavy chain containing a variable region as long as the variable region is identical, or at least 90% homologous, preferably at least 95% homologous, with the heavy chain variable region of the antibody of the invention.

In general, the antigen-binding properties of an antibody can be described by three specific regions located in the heavy chain variable region, referring as variable regions (CDRs), and separated into four framework regions (FRs). The sequences of four FRs amino acids are relatively conservative and do not directly participate in the binding reaction. A cyclic structure are formed by these CDRs which are close to each other in the spatial structure by the β-folds formed by the FRs between them, and the CDRs on the heavy chains and the CDRs on the corresponding light chains constitute the antigen-binding sites of the antibody. The amino acid sequence of the same type of antibody can be used to determine which amino acids have constituted the FR or CDR region.

The variable regions of the heavy chains and/or light chains of the antibodies of the invention are of particular interest because at least parts of them are involved in binding to a antigen. Thus, the invention encompasses those molecules having an antibody heavy chain and light chain variable region with CDRs as long as their CDRs have a homology of more than 90% (preferably more than 95%, optimally more than 98%) to the CDRs identified herein.

The invention includes not only intact antibodies but also fragments of antibodies with immunological activity or fusion proteins formed by antibodies with other sequences. Accordingly, the invention also includes active fragments, derivatives and analogs of said antibodies.

As used herein, the terms "fragments", "derivatives" and "analogs" refer to the polypeptides that substantially maintain the same biological function or activity of the antibodies of the invention. The polypeptide fragments, derivatives or analogs of the present invention may be (i) a polypeptide with one or more conservative or non-conservative amino acid residues (preferably the conservative amino acid residues) being substituted, while such a substituted amino acid residue may or may not be encoded by a genetic code, or (ii) a polypeptide having substituted group(s) in one or more amino acid residues, or (iii) a polypeptide formed by fusion of the mature polypeptide with another compound (such as the compound that prolongs the half life of the polypeptide, such as polyethylene glycol), or (iv) a polypeptide with additional amino acid sequence fused to said polypeptide sequence, such as fusion proteins formed by fusion with leader sequence, secretion sequence or sequence used to purify the polypeptide, or a fusion protein formed with a 6His tag. According to the teachings of the present application, these fragments, derivatives and analogs are within the scope commonly known by the skilled person.

An antibody of the present invention refers to a polypeptide comprising the CDRs regions having HPV16E protein binding activity. The term also includes a variant form of the polypeptide comprising the above CDRs regions having the same function as the antibodies of the invention. These variations include, but are not limited to, deletion, insert and/or replacement of one or more amino acids (typically 1-50, preferably 1-30, more preferably 1-20, most preferably 1-10), and adding one or more (typically 20 or less, preferably 10 or less, more preferably 5 or less) amino acids at the C-terminus and/or N-terminus. For example, in the art, replacement with similar or similar amino acids does not normally alter the function of the protein. Also, for example, the addition of one or several amino acids at the C-terminus and/or the N-terminus will not normally alter the function of the protein. The term also includes the active fragments and active derivatives of the antibodies of the invention.

The mutated forms of the polypeptide include homologous sequences, conserved variants, allelic variants, natural mutants, induced mutants, proteins encoded by DNA that hybridizes to the encoded DNA of the antibodies of the invention under high or low stringency conditions, and polypeptides or proteins obtained using antisera against antibodies of the invention.

The present invention also provides other polypeptides, such as fusion proteins comprising a human antibody or a fragment thereof. In addition to the substantially full length polypeptides, the present invention also encompasses fragments of antibodies of the invention. Typically, the fragment has at least about 50 consecutive amino acids of the antibody of the invention, preferably at least about 50 consecutive amino acids, more preferably at least about 80 consecutive amino acids, and most preferably at least about 100 consecutive amino acids.

In the present invention, the "conserved variants of the antibodies of the present invention" refers to the polypeptides formed by replacing at most 10, preferably at most 8, more preferably at most 5, and most preferably 3 amino acid of the amino acid sequence of the polypeptide of the present invention with the amino acid having similar or analogous property. These conservative variant polypeptides are preferably formed by carrying out the amino acid replacement according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

The present invention also provides a polynucleotide molecule encoding the above antibody or fragment thereof or a fusion protein thereof. The polynucleotides of the present invention can be in a form of DNA or RNA. DNA includes cDNA, genomic DNA, or synthetic DNA. DNA may be single-stranded or double-stranded. DNA may be the coding strand or non-coding strand. The sequences of coding regions for coding mature polypeptides could have same sequences or degenerate variants of SEQ ID NO.: 3, 5, 7, 9, 13, 15, 17 and 19. As used herein the term 'degenerate variant' refers to nucleic acid sequences encoding the same amino acid sequence with the polypeptides of the invention but different with the coding regions of SEQ ID NO.: 3, 5, 7, 9, 13, 15, 17 and 19.

The polynucleotide encoding the mature polypeptide of the present invention includes coding sequences encoding only mature polypeptides; coding sequences of mature polypeptides and various additional coding sequences; coding sequences (and optional additional coding sequences) of mature polypeptides and non-coding sequences.

The term "polynucleotide encoding the polypeptide" may be a polynucleotide that encodes the polypeptide, or a polynucleotide that also includes additional coding and/or non-coding sequences.

The present invention also relates to a polynucleotide that hybridize to the sequence described above and that have at least 50%, preferably at least 70%, more preferably at least 80% identity between the two sequences. In particular, the present invention relates to a polynucleotide that is hybridizable to the polynucleotide of the invention under stringent conditions. In the present invention, "stringent conditions" means: (1) hybridization and elution at lower ionic strength and higher temperature, such as 0.2×SSC, 0.1% SDS, 60° C.; or (2) hybridization in the presence of a denaturant such as 50% (v/v) formamide, 0.1% calf serum/0.1% Ficoll, 42° C. or the like; or (3) hybridization occurs only if the identity between the two sequences is at least 90%, more preferably 95% or more. And the polypeptide encoded by the hybridizable polynucleotide has the same biological function and activity as the mature polypeptide shown in one of SEQ ID NO: 12 and/or SEQ ID NO.: 22.

The full-length nucleotide sequence of the present invention or a fragment thereof can usually be obtained by the methods include but are not limited to PCR amplification, recombination or synthetic methods. A viable approach is to synthesize the relevant sequence in a synthetic manner, especially when the fragment length is short. In general, a very long fragment can be obtained by first synthesizing multiple small fragments and then ligating them. In addition, the coding sequence of the heavy chain and the expression tag (e.g., 6His) can be fused together to form a fusion protein.

Once the relevant sequence is obtained, the relevant sequence can be obtained in bulk using the recombination method. It is usually cloned into a vector, transferred to a cell, and then isolated from the host cell after proliferation by conventional methods. The biomolecules (nucleic acids, proteins, etc.) involved in the present invention include biomolecules present in separate form.

At present, DNA sequences encoding the protein of the invention (or fragments thereof, or derivatives thereof) can be completely obtained by chemical synthesis. The DNA sequence can then be introduced into a variety of existing DNA molecules (or vectors) and cells known in the art. In addition, mutations can also be introduced into the protein sequences of the present invention by chemical synthesis.

The present invention also relates to a vector comprising the suitable DNA sequence as described above and a suitable promoter or control sequence. These vectors can be used to transform suitable host cells to enable them to express proteins.

Host cells can be prokaryotic cells, such as bacterial cells; or lower eukaryotic cells, such as yeast cells; or higher eukaryotic cells, such as mammalian cells. Representative examples include: bacterial cells such as *Escherichia coli, Streptomyces; Salmonella typhimurium*; fungal cells such as yeast; insect cells such as *Drosophila* S2 or Sf 9; animal cells such as CHO, COS7, 293 cells.

Transformation of host cells with recombinant DNA can be carried out using conventional techniques well known to those skilled in the art. When the host is a prokaryote such as *E. coli*, competent cells capable of absorbing DNA can be harvested after the exponential growth phase and treated with the $CaCl_2$. The steps used are well known in the art. Another method is using $MgCl_2$. If necessary, the transformation can also be carried out by electroporation. When the host is a eukaryote, the following DNA transfection methods are available: calcium phosphate coprecipitation, conventional mechanical methods such as microinjection, electroporation, liposome packaging, and the like.

The obtained transformants can be cultured in a conventional manner to express the polypeptides encoded by the genes of the present invention. Depending on the host cell used, the medium used in the culture may be selected from a variety of conventional media. And the host cells are cultured under conditions suitable for the growth. After the host cells grow to the appropriate cell density, the selected promoter is induced with a suitable method, such as temperature conversion or chemically induced, and the cells are cultured for a further period of time.

The recombinant polypeptide in the above method can be expressed intracellularly, or on the cell membrane, or secreted out of the cell. If desired, recombinant proteins can be isolated and purified by various separation methods using their physical, chemical and other properties. These methods are well known to those skilled in the art. Examples of such methods include, but are not limited to, conventional renaturation treatments, treatment with a protein precipitant (salting-out method), centrifugation, osmosis cell disruption, super-treatment, ultracentrifugation, molecular sieve chromatography (gel filtration), adsorption chromatography, ion-exchange chromatography, high performance liquid chromatography (HPLC) and various other liquid chromatography techniques and combinations of these methods.

The antibodies of the invention may be used alone or in combination with or couple with a detectable label (for diagnostic purposes), a therapeutic agent, a PK (protein kinase) modified moiety, or any combination thereof.

A detectable label for diagnostic purposes include, but are not limited to, fluorescent or luminescent labels, radiolabels, MRI (magnetic resonance imaging), or CT (computerized tomography) contrast agents, or enzymes capable of producing detectable products.

Therapeutic agents that can be associated with or coupled with the antibodies of the present invention include, but are not limited to: 1. Radioactive nuclide (Koppe, et al, 2005, *Cancer metastasis reviews* 24, 539); 2. Biological toxin (Chaudhary et al, 1989, Nature, 339, 394; Epel et al, 2002, *Cancer immunology and immunotherapy* 51,565); 3. Cytokine such as IL-2 and the like (Gillies, et al, 1992, PNAS, 89, 1428; Card, et al, 2004, *Cancer immunology and immunotherapy* 53, 345; Halin, et al, 2003, *Cancer research* 63, 3202); 4. Gold nano-particle/nano-rod (Lapotko, et al, 2005, *Cancer letters* 239, 36; Huang, et al, 2006, *Journal of the American chemical society* 128, 2115); 5. Virus particles (Peng, et al, 2004, *Gene therapy*, 11, 1234); 6. Liposome (Mamot, et al, 2005, *Cancer research* 65, 11631); 7. Magnetic nano-particles; 8. Prodrug activating enzymes (such as DT-diaphorase (DTD) or Biphenyl hydrolase-like protein (BPHL)); 10. Chemotherapeutic agent (e.g., cisplatin) or any form of nanoparticles and the like.

The present invention also provides a composition. In a preferred embodiment, the composition is a pharmaceutical composition comprising the above-described antibody or active fragment thereof or a fusion protein thereof, and a pharmaceutically acceptable carrier. In general, these materials may be formulated in a non-toxic, inert and pharmaceutically acceptable aqueous carrier medium, wherein the pH is generally about 5 to 8, preferably about 6 to 8, although the pH may vary depending on the nature of the substance to be formulated, and the condition to be treated. The formulated pharmaceutical compositions may be administered by conventional routes, including, but not limited to, intratumoral, intraperitoneal, intravenous, or local drug delivery.

The pharmaceutical compositions of the present invention can be used directly to bind with HPV16 E7 protein molecules and are therefore useful for the prevention and treatment of tumors. In addition, other therapeutic agents may be used at the same time.

The pharmaceutical composition of the present invention contains a monoclonal antibody (or a conjugate thereof) of the present invention in a safe and effective amount (e.g., 0.001 to 99 wt % by weight, preferably 0.01 to 90 wt % by weight, more preferably 0.1 to 80 wt % by weight) and an acceptable carrier or excipient. Such carriers include, but are not limited to, saline, buffer, glucose, water, glycerol, ethanol, and combinations thereof. The pharmaceutical preparation should match the method of administration. The pharmaceutical compositions of the present invention may be prepared into the form of injections, for example, saline or aqueous solutions containing glucose and other adjuvants are prepared by conventional methods. Pharmaceutical compositions such as injections, solutions should be made under aseptic conditions. The amount of the active ingredient is a therapeutically effective amount, such as about 1 microgram/kg body weight per day to about 5 mg/kg body weight per day. In addition, the polypeptides of the present invention may also be used with other therapeutic agents When a pharmaceutical composition is used, a safe and effective amount of an immunoconjugate is administered to a mammal wherein the safe effective amount is generally at least about 10 micrograms per kilogram of body weight and, in most cases, no more than about 8 milligrams per kilogram of body weight, preferably, the dose is from about 10 micrograms per kilogram body weight to about 1 milligram per kilogram of body weight. Of course, the route of administration, the patient's health and other factors, should be considered for the specific dose, which are within the scope of skills of skilled practitioners.

Hybridoma Cell Strain

The invention also provides the hybridoma cell strains which are able to produce monoclonal antibodies against HPV16 E7 proteins; preferably, the invention also provides a high-titer hybridoma cell strains which are able to produce monoclonal antibodies efficiently against HPV16 E7 proteins.

After the hybridoma producing the HPV16 E7 protein monoclonal antibodies is obtained, it is convenient to prepare antibodies by the hybridoma. Additionally, it is convenient to learn the structures of the antibodies of the invention (e.g. VL and VH of the antibodies), then recombination methods could be used to prepare monoclonal antibodies of the invention.

Preparation of Monoclonal Antibodies

The antibodies of the invention could be prepared through various kinds of methods which is known to people in this field, for instance, the antigens of the invention could be applied to animals to induce the production of monoclonal antibodies. For antibodies, hybridoma technique could be used to prepare (Kohler et al., Nature 256; 495, 1975; Kohler et al., Eur. J. Immunol. 6:511, 1976; Kohler et al., Eur. J. Immunol. 6:292, 1976; Hammerling et al., In Monoclonal Antibodies and T Cell Hybridomas, Elsevier, N.Y., 1981) or by recombinant DNA technique (U.S. Pat. No. 4,816,567).

Characteristic myeloma cells are those that fuse efficiently, support stable high-level production of antibody by the selected antibody-producing cells, and are sensitive to a medium such as HAT medium, including myeloma cell lines such as murine myeloma lines, including those derived from MOPC-21 and MPC-11 mouse tumors (available from the Salk Institute Cell Distribution Center, San Diego, Calif. USA), and SP-2, NZO, or X63-Ag8-653 cells (available from the American Type Culture Collection, Rockville, Md. USA). Human myeloma and mouse human heteromyeloma cell lines also have been described for the production of human monoclonal antibodies [Kozbor, J. Immunol., 133: 3001 (1984); Brodeur et al., Monoclonal Antibody Production Techniques and Applications, pp. 51-63 (Marcel Dekker, Inc., New York, 1987)].

Culture medium in which hybridoma cells are growing is assayed for the production of monoclonal antibodies having the requisite specificity, for example by an in vitro binding assay such as enzyme-linked immunoabsorbent assay (ELISA) or radioimmunoassay (RIA). The location of the cells that express the antibody may be detected by FACS. Thereafter, hybridoma clones may be subcloned by limiting dilution procedures and grown by standard methods (Goding, Monoclonal Antibodies: Principles and Practice, Academic Press (1986) pp. 59-103). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional purification procedures for example protein A-Sepharose, hydroxylapatite chromatography, gel electrophoresis, dialysis, or affinity chromatography.

The invention provides a type of monoclonal antibodies against HPV E7 proteins and especially against HPV16 E7 proteins. In a preferred embodiment of the invention, monoclonal antibodies are prepared by hybridoma cultivation. The supernatant of hybridoma cultivation is taken and unrefined IgG was obtained by saturated ammonium sulfate precipitation. Then the unrefined IgG is purified by affinity column Protein G-Sepharose.

In a preferred embodiment of the invention, monoclonal antibodies are obtained using Balb/C mouse ascites for the production of monoclonal antibodies. The hybridoma cells are inoculated into sensitized mouse abdominal cavity and the abdominal cavity shows obvious swelling after 10 days. The ascites is extracted and crude extracted by saturated ammonium sulfate precipitation. Then the unrefined antibodies are purified by affinity column Protein G-Sepharose.

Labeled Immunoglobulin

In a preferred embodiment of the invention, the immunoglobulin has a detectable label. Preferably, the label is selected from the group consisting of a colloidal gold label, a colored marker and a fluorescent label.

Colloidal gold labels can be carried out using methods known to those skilled in the art. In a preferred embodiment of the invention, the monoclonal antibody of the HPV E7 protein is labeled with colloidal gold to obtain a colloidal gold-labeled monoclonal antibody.

The HPV E7 protein monoclonal antibody of the invention has good specificity and high titer.

Detection Plates and Materials

The detection plates of the invention could be produced from conventional detection plate materials and produced by conventional methods.

The HPV16 E7 proteins immune detection plate of the invention includes test strips and support plate like PVC plate for holding the strips; the described test strips are lapped orderly by filter papers, chromatography materials, nitrocellulose membranes and bibulous papers. Lap positions could be fixed by conventional material like adhesive tape; Chromatography materials are coated by HPV16 E7 proteins monoclonal antibodies and polyclonal antibodies with colloidal gold labels and colored labels. Nitrocellulose membranes could absorb detection lines and control lines.

In a preferred embodiment of the invention, the concentration of HPV16 E7 proteins monoclonal antibody coats in chromatography materials is 0.5-1.5 mg/ml and the coating amount is 50 µl/cm². The optimal concentrations are 0.5 or 1.5 mg/ml, 50 µl/cm².

Detection Method and Results Determination

Flatwise the detection plate, add about 120 µl of sample on the filter paper and observe the results in 3 to 5 minutes. Determine the results from the positions of stripes.

Negative: color marking appears in quality control area, and detection area showing negative.

Positive: color marking only appears in quality control area but disappears in detection area showing positive.

Invalid: color marking disappears in both area or appears in detection area and disappears in quality control area showing wrong detection method or degenerative or disabled detection plate and detection plate should be changed.

Methods and Samples

This method relates to the cervical cancer detection using dissolved cell and/or tissue sample. The rough procedures as follows: obtain the cell and/or tissue samples; dissolve samples in medium; detect the level of HPV oncoprotein in dissolved sample. The sample of this method could be any samples exist in sell preservation liquid including cells like the samples used in liquid-base cytology.

The invention could be used in detection of HPV oncoproteins in HPV infection-related cancers. HPV infected cancers include genitourinary tumors such cervical cancer, bladder cancer, endometrial cancer, penile carcinoma etc., and the early stages of cancers like small cell lung cancer, melanoma, head and neck cancer.

According to the invention, using HPV oncoprotein molecular marks is able to support or even replace cytological and/or histological detection. In special cases, protein molecular marks could be used as a diagnostic tool but with no need for further support which bases on cellular morphology. Under the condition without the support bases on cellular information, diagnosing cancer only in protein molecule level is limited to cases. Among them, marks or mark level should be specific to detection conditions. The biological mark used in the invention is HPV oncoproteins which are derived in virus, because the marking features of virus will not show in uninfected tissues. Therefore, the detection of HPV infection could be conducted in sample solution.

The samples used in the invention include cells, tissue samples and biopsy specimen. The term 'biopsy' should include all types of biopsy known in this field. Biopsies as used in the context of the present invention may comprise e.g. resection samples of tumors, tissue samples prepared by endoscopic means or punch- or needle-biopsies of organs.

Samples as used in the context of the present invention may comprise fixed or preserved cell or tissue samples. Cell or tissue samples may e.g. be preserved in a standard sample collection, storage or transportation solution, known to those of skill in the art such as e.g. commercially available preservation solutions (formalin solution, Cytyc "Preserve-Cyt", or Tripath Imaging "Cytorich", etc.). Those solutions may contain one or more alcohols, aldehydes, ketones, acids, metal-ions or sublimates, ethers etc. for preservation of cellular components. Alcohols include methanol, ethanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample solutions include organic acids (acetic acid, trichloro-acetic acid, salicylic acid, picrinic acid) or inorganic acids such as chromic acid. Standard sample solutions may comprise metals such as silver, copper, chromium, mercury, osmium, uranium. Solutions of salts such as uranyl-acetate, potassium-bichromate, ammonium sulfate, etc. may be components of preservative solutions.

Additionally, in the disclosed method described in this application, samples which conduct cell lysis immediately after obtaining could be used. Using the samples lysed immediately after obtaining, morphological information is lost in this process but protein molecular information is saved. Samples could be transferred to solution contains suitable detergent and conservant from the body of individuals. Choosing suitable agents for lysis mediums could preserve the molecular fraction of raw materials and prevent degradation, for instance, using enzyme inhibitor could minimize the degradation of enzyme activity. Therefore, the detected sample solution in lysis solution could detect protein molecular properties of samples in dissolving process.

According to the present invention, the samples may be solubilized in any suitable solvent. Such solvents may for example be aqueous solutions of chaotropic agents such as e.g. urea, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isothionates, sucrose esters), cationic detergents (e.g. cetyl trimethylammonium chloride), non-ionic detergents (e.g. Tween 20, Nonidet P-40, Triton X-100, NP-40, Igepal CA-630, N-Octyl-Glucosid) or amphoteric detergents (e.g CHAPS, 3-Dodecyl-dimethylammonio-propane-1-sulfonate, Lauryl dimethylamine oxide) and/or of alkali hydroxides such as e.g. NaOH or KOH. Generally any suitable liquid may be used as a solvent in the lysis buffer of the present invention. The liquid may be organic or inorganic and may be a pure liquid, a mixture of liquids or a solution of substances in the liquid and may contain additional substances to enhance the properties of the solvent. In certain embodiments, The formulation of the lysis medium is 50 mM Tris-HCl, 150 mM NaCl, 1% NP-40, 0.5% sodium deoxycholate, 0.1% SDS.

The lysis mediums for dissolving samples could contain one or more than one reagents which prevent the component decomposition of material. The components include enzyme inhibitors like protease inhibitors. In the embodiment of the invention, samples lysed directly. The protease inhibitors could include serpins, cysteine protease inhibitors, aspartic protease inhibitors, metalloproteinase inhibitors, acid protease inhibitors, base protease inhibitors or neutral protease inhibitors. In the embodiment of the invention, the protease inhibitors were pepstatin, leupeptin, aprotinin and 100 µg/ml PMSF.

Reagent Kit

The present invention also provides a kit for containing an antibody (or a fragment thereof) or a detection plate of the present invention. In a preferred embodiment of the present invention, the kit further comprises a container, an instruction for use, a buffer agent and so on.

A detection kit is further designed according to the present invention for detecting HPV oncoprotein levels, said kit contains antibodies that recognize the HPV oncoprotein, a lysis medium for dissolving the sample, general reagents and buffers desired for detection, such as various buffers, detection labels, detection substrates and so on. The antibody is preferably an anti-HPV E7 antibody, more preferably an anti-HPV16 E7 antibody. The assay kit may be an in vitro diagnostic device.

This reagent kit is further designed and developed to be able to diagnose HPV infection status in sample solution. This reagent kit could be used to detect HPV oncoproteins in sample solution and the cell preservation liquid could be the cell preservation liquid used in liquid based cytology detection. The reagent kits and vitro-detection instruments are used to dissolving cells in suitable lysis mediums and develop detecting HPV infection tumor in dissolved samples based on cellular analysis.

The purpose of the invention is to provide a method for detecting HPV16 E7 protein expression which can be used to detect HPV infection related cancers, especially cervical cancer.

The inventor of the invention produced a monoclonal antibody 7B6 specific to human papilloma virus HPV16 E7 protein and studied its activity. The antigen epitope peptide of this monoclonal antibody is between amino acid No. 100 to 109 and includes an amino acid sequence of DEIDG. This sequence is highly homologous in E7 among HPV16, and HPV18. Therefore, 7B6 and HPV18 E7 have slightly a cross reaction. The immunocytochemical staining of HPV non-expressed cervical cancer cell line C-33A, HPV16 E7 expressed cervical cancer cell line CaSki and HPV18 E7 expressed cervical cancer cell line Hela by using this anti-HPV16 E7 monoclonal antibody 7B6, has shown that 7B6 has strong stain reaction with HPV16 E7 positive cells CaSki, weak stain reaction with HPV18 E7 positive cells Hela and no reaction with C-33A cells which has no expression of HPV proteins.

Furthermore, the inventors of the invention have used the prepared anti-HPV16 E7 monoclonal antibody 7B6 to conduct immunocytochemical staining of cervical cancer cells which were fixed with 4% paraformaldehyde or LBC stationary liquid for several days. HPV16 E7 expression was not detected in cervical cancer stains C-33 without any HPV DNA. When CaSki cells and C-33A cells were mixed with different ratios (1:9 or 1:99) and the ratio of positive tumor cells was as low as 1%, 7B6 could specifically detect existence of tumor cells by detecting HPV16 E7 inside of cancer cells. Additionally, two types of stationary liquid had no affect on positive or negative results. According to the observation, the inventors of invention have finished this invention.

Therefore, the method of invention is a method for detecting tumor marker which comprises a step of detecting HPV16 E7 in a sample.

In the method of the invention, the sample to be detected preferably comprises cast-off cells collected from a subject, culture of issue or section of issue. Samples can also be a tissue collected from a subject, or suspension cells prepared from culture of said tissue. Additionally, the preferred cell is cast-off cell of cervical cancer.

In the method of invention, the subject may be a patient possibly suffered from cervical lesions, or a patient suffered from cervical diseases.

Preferably, the HPV16 E7 is HPV16 E7 protein or a fragment thereof. In this situation, detecting HPV16 E7 preferably comprises conducting an immunocytochemical staining of HPV16 E7. The useful anti-HPV16 E7 antibody preferably is a monoclonal antibody against HPV16 E7 and more preferably, is a mouse anti-HPV16 E7 monoclonal antibody produced by hybridoma 7B6 or a monoclonal antibody which has same binding activity as that of said mouse anti-HPV16 E7 monoclonal antibody.

In the described immunodetection, the protein expressed by HPV16 E7 oncogene is used as a reliable marker for an HPV-related malignant or pre-malignant cytogenesis. One of the most useful aspects of the invention is an application in diagnosis of cervical cancer, squamous cells, adenocarcinoma and any abnormal epithelial cells related to carcinogenic HPV16 infection. The carcinogenic HPV16 infection comprises koilocytosis; hyperkeratosis; precancer diseases such as intraepithelial neoplasia or intraepithelial lesions; highly dysplasia and invasive or malignant cancers. In addition to cervical cancer, HPV16 E7 detection is also useful for detecting urinary reproductive system tumors such as bladder cancer, endometrial cancer and penile cancer, small-cell lung cancer, melanoma or head and neck cancer.

Another purpose of invention is to provide a kit. This kit can be a kit for diagnosis or a kit for research.

The kit of invention is used to detect a tumor marker wherein it contains an anti-HPV16 E7 monoclonal antibody. Preferably, the kit contains general reagents and buffers which are needed in detection, e.g., various buffers, detection labels and detection substrates. Preferably, the antibody is an anti-HPV16 E7 antibody and more preferably an anti-HPV16 E7 monoclonal antibody, and particularly preferably a mouse anti-HPV16 E7 monoclonal antibody produced by hybridoma 7B6 or a monoclonal antibody which has the same binding activity as that of said mouse anti-HPV16 E7 monoclonal antibody.

This invention also provides a method to distinguish HPV16 E7 infected tumor cells and tumor cells containing no HPV DNAs by detecting endogenous HPV16 E7 protein in cells. The basis of this method is that HPV16 E7 positive tumor cells are correctly detected even when the ratio of positive cells to total cells is 1% and when cells are fixed by LBC fixation liquid that is commonly used in clinical, positive cells can still be correctly detected. Therefore, it can conduct diagnosis of cancer at early stage so as to benefit early treatment.

Further, the invention provides a detection kit using said detection method.

The Main Advantages of the Present Invention Include:

(1) The invention provides antibodies against HPV E7 proteins having high specificity and strong affinity, and can be prepared in large quantities, and the quality of monoclonal antibody is easy to control.

(2) The antibodies against HPV E7 could combine with HPV16 E7 proteins and HPV18 E7 proteins but with significantly different binding activities. Therefore, these antibodies can not only detect HPV E7 proteins (including HPV16 E7 proteins and HPV18 E7 proteins), but also can identify different HPV types.

(3) The invention provides the method for detecting the HPV E7 protein by using the antibody provided by the invention having good stability, high detection sensitivity, and the binding affinity of the antibody with the HPV16 E7 protein reached 0.64 nM, and the binding affinity of the antibody with the cervical cancer cell line CaSki reached 1.52 nM.

(4) The present invention provides monoclonal antibodies as well as detection methods suitable for early diagnosis of related cancers and large-scale patient screening and can be used to monitor recurrent patients.

The invention is further illustrated by the following examples. It should be appreciated that these examples are only intended to illustrate the invention, but not to limit the scope of the invention. Unless indicated otherwise, all percentage and parts are calculated by weight.

Materials

1. The cells and the main reagents involved in the following examples: human cervical cancer cell lines Hela, myeloma cells SP2/0 and CaSki cells, C-33A cells purchased from Chinese Academy of Sciences cell bank. 6-8 weeks BALB/c mice purchased from animal experimental center of Yangzhou University. RMPI 1640, DMEM, fetal calf serum purchased from Hyclone Company. 0.25% pancreatin purchased from Gibco Invitrogen Company. EZ-Link TMSulfo-NHS-LC-Biotin and labeling Kits Product#21327 purchased from Thermo Scientific Company. Sodium deoxycholate, BSA, SDS, TMB, Tween-20 purchased from Amresco. Others conventional chemical reagents are purchased from Sinopharm Chemical Reagent Limited Company and other biological materials are all commercially available if it without special explanation.

2. The main instruments involved in the following examples: MULTISKAN MK3 ELISA (Thermo Company); WellWASK4 MK2 Microplate Washer (Thermo Company); ELISA Plate (COSTAR Company).

Example 1

1 Preparation of Human Papilloma Virus HPV16 E7 Monoclonal Antibody.

1.1 Animal Immunization 6-8 weeks of female BALB/C mice, GST-HPV16 E7 protein of immunogen, immune procedures can be seen from Table 1. Mice tails were cut and blood was collected before each immunization. GST-HPV16 E7 was used as detectable antigen coatings for detecting serum titers of mice by indirect ELISA method. When the serum titers of mice reached the maximum and no longer increased, splenocytes were fused.

TABLE 1

Immunization Procedure for Mice

| Immune Time | Immunogen | Immunizing Dosages (Protein/volume) | Immunization Route |
|---|---|---|---|
| First Immune (first day) | GST-HPV16 E7 + complete adjuvant | 100 μg/0.1 ml | Intraperitoneal injection |
| Second Immune (day 21) | GST-HPV16 E7 + incomplete adjuvant | 50 μg/0.1 ml | Back subcutaneous multipoint injection |
| Third Immune (day 35) | GST-HPV16 E7 + incomplete adjuvant | 50 μg/0.1 ml | Back subcutaneous multipoint injection |
| Fourth Immune (day 49) | GST-HPV16 E7 + incomplete adjuvant | 50 μg/0.1 ml | Back subcutaneous multipoint injection |
| Fifth Immune (day 63) | GST-HPV16 E7 + incomplete adjuvant | 50 μg/0.1 ml | Back subcutaneous multipoint injection |
| Sixth Immune (day 70) | GST-HPV16 E7 + normal saline | 50 μg/0.1 ml | Intraperitoneal injection |

1.2 Cell Fusion and the Culture of Cells

The splenocytes and myeloma cells SP2/0 were collected by conventional method and fused. The fused ratio of splenocyte: SP2/0 is 5:1 and the fused cells were divided and placed in culture plate with 96 holes, placed in 37° C., 5% $CO_2$ of constant temperature incubator for selective culture. After fusion, the whole medium was replaced with HAT medium three times; when the hybridoma cells were covered with a microscope, ELISA was performed.

1.3 Screening for the Positive Hybridoma

When detection was performed, indirect ELISA was used for screening: His-HPV16 E7 fusion protein was used as antigen, 2 μg/ml for package and 4° C. overnight. Washed with PBST and dried, then 5% skim milk powder was added for blocking, 37° C. for 2 hours or 4° C. overnight. After washed with PBST and dried, then supernatant of hybridoma was added and the positive (P), negative (N) and blank control (only the enzyme secondary antibody was added in blank control) were set, then reacted at 37° C. for 1 hour. Washed and dried with PBST, then goat-anti-mouse-HRP secondary antibodies (Sigma A2554) (1:10000) were added and reacted at 37° C. for 45-60 minutes. Washed with PBST and dried, then developed with TMB and stopped with 2M $H_2SO_4$.

As for the results of ELISA, the holes in which the OD value is greater than 0.6 were determined as positive holes and re-examination. If the results of two consecutive detection are both positive, the positive cells were amplified, frozen and subcloned.

1.4 Establishment of Hybridoma Cell Line

For those wells that are positive for the two screening, limiting dilution method was used to subclone. A 96-well cell culture plate was used and 150 μl HAT culture liquid was added into each well; the positive wells needed for subcloning were gently blown, beaten and suspended, then 100 μl of cell suspension solution was taken and added into the 96-well cell plate and doubling dilution was started from the first well. Cell counter was used for the wells which contain about 100 cells and added into the loading slot with 6 ml HAT culture solution, then added to the cell plate of feeding layer at 100 μl per wells in the first three rows; then 3 ml of HAT medium was added to the cell plate of feeding layer at 100 μl per wells in the middle of three rows; then 5 ml of HAT medium was added to the cell plate of feeding layer at 100 μl per wells in the latter of six rows. When the positive rate of each plate was calculated to reach 100%, the stable cell lines can be obtained. Then these cell lines were transferred into cell culture plates for the enlarged cultivation and frozen and stored.

1.5 Mass Production of Monoclonal Antibodies (Ascites Preparation)

The hybridoma cells (7B6) were mass cultured and 6-8 weeks of BALB/C female mice were treated with liquid paraffin for sensitization, then $1\times10^6$ hybridoma per mice was intraperitoneally injected. After ten days, when the abdomens of mice were obviously puffy, the ascites was extracted by No. 9 syringe needle. Obtained ascites was coated by His-HPV16 E7 and detected by ELISA with ascites titers of up to 1:10,000. After fibrous protein was removed and treated by salting out, purified by Protein G affinity column chromatography. The protein peak outflow was collected, phosphate buffer (PBS) was used for dialysis and ultraviolet spectrophotometer OD260, 280 were used to determine the antibody protein concentration as 0.7-1.5 mg/ml. The indirect ELISA detection results show: the titer of purified monoclonal antibody is above 1:10000.

The above methods for the preparation of HPV16E7 monoclonal antibodies were used by the inventor. 1500 of cell lines were screened and three stains (7B6, 1H11, 2G7) with better specificity and higher antibody titers were obtained. In the course of the experiment, the inventor used immune procedure for six times and 12 monoclonal cell lines were screened, among them, 8 stains were changed into negative after subcloning and 4 strains were still positive. Stable positive clones (7B6, 1H11, 2G7) were obtained after passage.

2. Identification of Monoclonal Antibody

2.1 Identification of Monoclonal Antibody Ig Subclass

The purified monoclonal antibody was diluted at 1:10000 with PBS and the procedures were performed according to the instruction book of subclass identify kit from Sigma Company. The monoclonal antibody 7B6 was IgG2B.

1.2 Detection for Specificity and Cross Reaction of Monoclonal Antibody his-HPV16 E7 by ELISA His-HPV16 E7 (amino acid sequence of HPV16 E7, SEQ ID NO: 1) and His-HPV18 E7 (amino acid sequence of HPV18 E7, SEQ ID NO: 2), GST-HPV16 L2 fusion protein were used as antigens, respectively, =2 µg/ml for package and 4° C. overnight. Washed with PBST and dried, then 5% skim milk powder was added for blocking, placed it at 37° C. for 2 hours or 4° C. overnight. Washed with PBST and dried, then anti-HPB16 E7 monoclonal antibodies 7B6 (1 µg/ml) was added and reacted at 37° C. for 1 hour. Washed with PBST and dried, then goat-anti-mouse-HRP secondary antibodies (Sigma A2554) (1:10000) were added and reacted at 37° C. for 45-60 minutes. Washed with PBST and dried, then developed with TMB=and stopped with 2M $H_2SO_4$, Read at the position of OD450 nm. The results are shown in FIG. 1: 7B6 can combine with recombinant protein of HPV16 E7 and HPV18 E7 simultaneously but without the combination of HPV16 L2, that is, 7B6 can identify the same antigen peptide of HPV16 E7 and HPV18 E7.

Figure 2:
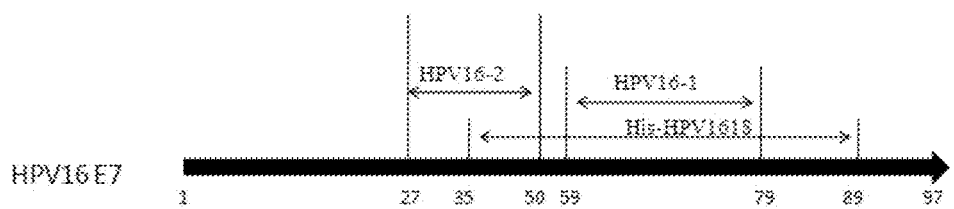
FIG. 2 shows the ELISA results of combination between HPV16 E7 monoclonal antibody and amino acid sequences of antigen epitopes. Experimental details are in Example 1, Section 2.3 of part.
Figure 2:
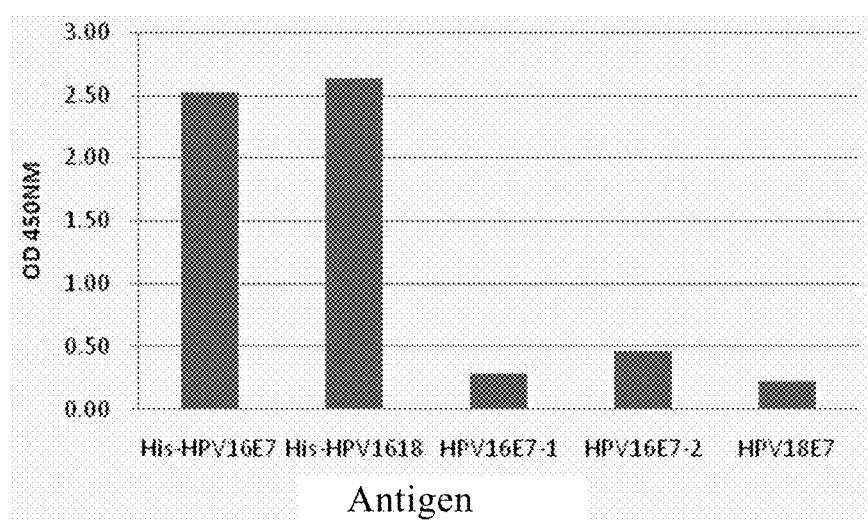

2.3 Analysis of Antigen-Binding Site of Anti-HPV16 E7 Monoclonal Antibodies Identification of the amino acid sequences of epitopes of monoclonal antibodies in HPV16 E7 antigen proteins. ELISA was used for the identification: polypeptides or recombinant proteins were used as antigens, wherein polypeptides were HPV16 E7-1 (amino acid sequence of SEQ ID NO: 23, KCDSTLRLCVQSTHVDIRTLE) and HPV16 E7-2 (amino acid sequence of SEQ ID NO: 24, LNDSSEEE-DEIDGPAGQAEPDRAH) respectively, recombinant proteins were His-HPV16168 (amino acid sequence of SEQ ID NO: 25, DEIDGPAGQAEPDRAHYNIVTFCCKCDSTLR-LCVQSTHVDIRTLEDLLMGTLGIV) and His-HPV16 E7, respectively. 4 µg/ml protein antigens for package, 2 µg/ml polypeptide antigens for package and 4° C. overnight. Washed with PBST and dried, then 5% skim milk powder was added for blocking, placed it at 37° C. for 2 hours or 4° C. overnight. Washed with PBST and dried, then anti-HPB16 E7 monoclonal antibodies 7B6 (1 µg/ml) was added and reacted at 37° C. for 1 hour. Washed with PBST and dried, then goat-anti-mouse-HRP secondary antibodies (Sigma A2554) (1:10000) were added and reacted at 37° C. for 45-60 minutes. Washed with PBST and dried, then developed with TMB and stopped with 2M $H_2SO_4$. Read at the position of OD450 nm. The results are shown in FIG. 2: due to 7B6 can combine with recombinant protein His-HPV1618 and polypeptide HPV16 E7-2, according to the amino acid sequence shown in FIG. 2(A), the amino acid region for the combination of 7B6 and HPV16 E7 can be at position 35-50. Because cross reaction can be present in the 7B6 can and recombinant protein HPV18 E7, which means 7B6 can identify homologous sequence of HPV16 E7 and HPV18 E7. Therefore, the amino acid sequence identified by 7B6 is DEIDG, that is, the amino acid at position 35-39 of HPV16 E7.

2.4 Gene Cloning of Clonal Antibody and Sequencing

2.4.1 Extracting of Total RNA of Hybridoma Cells

Referred to Invitrogen 'TRIZOL Reagent' operation manual to extract total RNA of hybridoma cells.

2.4.2 Reverse Transcription and Clonal Sequencing of Antibody Genes

Referred to Fermantas 'RevertAid First Strand cDNA Synthesis Kit' instruction manual to conduct reverse transcription. 5' and 3' end primers were designed and synthesized, the obtained cDNA was used as template to amplify antibody genes, the condition of reaction is as follows:

94° C., 1 min; 94° C., 30 s; 55° C., 30 s; 72° C., 1 min (30 cycles); 72° C., 5 min. After the PCR product bands were obtained and linked to pMD-19T vector, transferred into TOP10 competent cells, coated onto LB plate with IPTG, X-gal and then blue-white spot screening culture was conducted (37° C., overnight). The white single colony was selected and inoculated to 2 ml LB culture medium (Amp+). After stayed overnight at 37° C., the DNA of bacterial liquid was extracted and sequenced. The results are shown in FIG. 3,

2.5 Affinity Analysis of Binding of Anti-HPV16 E7 Monoclonal Antibody

Figure 4:
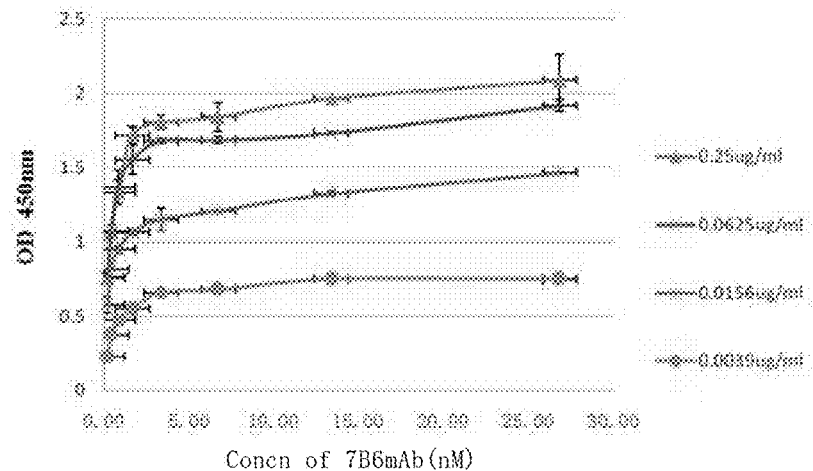
FIG. 4 shows the ELISA results of protein binding affinities analysis of HPV16 E7 monoclonal antibody. Experimental details are in Example 1, Section 2.5: the coating concentrations of His-HPV16 E7 are 0.25 µg/ml, 0.0625 µg/ml, 0.0156 µg/ml, 0.0039 µg/ml. The incubating concentrations of 7B6 are dealt with double dilution then obtain 8 gradients. Obtained values are plugged into $K_{aff}=(n-1)/2$ (n [Ab']−[Ab]) to get 6 values of K, then calculate for average value. Lastly the average protein level affinity of 7B6 is 0.64 nM.

Binding affinity constant of monoclonal antibody proteins was determined according to the method by Beatty et al. (J. David Beatty, Barbara G. Beatty and William G. Vlahos 1987). His-HPV16 E7 protein was coated with different concentrations: 0.25 µg/ml, 0.0625 µg/ml, 0.0156 µg/ml, 0.0039 µg/ml and the concentration ratio is 1:4:16:64. The added first antibody was 7B6 antibody and the concentration was doubling diluted from the concentration of 2 µg/ml. There were total 8 gradients and then ELISA test was conducted. The obtained values were plot into $K_{aff}=(n-1)/2(n[Ab']-[Ab])$ to obtain the affinity constant. [Ab'] and [Ab] in the equation represent the antibody concentration which has half-light absorption value when the concentration of antigen is Ag or Ag'. It means using the antibody concentration corresponding to half of the highest OD value (50% OD) on the curve through graphing method. In this equation, n=Ag/Ag'. Then each two of them were compared, when n=4, three K values could be obtained, when n=16, two K values could be obtained and when n=64, one K values could be obtained then calculate the average of these six values as the result. The results are shown in FIG. 4: the binding affinity of 7B6 and recombinant protein His-HPV16 E7 is 0.64 nM.

The above method was used to calculate the binding affinities of 1H11, 2G7 with recombinant protein His-HPV16 E7 of 3.48 nM and 1.13 nM respectively. It could be seen from the above results that the binding affinity of 7B6 is five times over 1H11, twice over 2G7.

2.6 Analysis of Anti-HPV16 E7 Monoclonal Antibody Cell Binding Affinity

Figure 5:
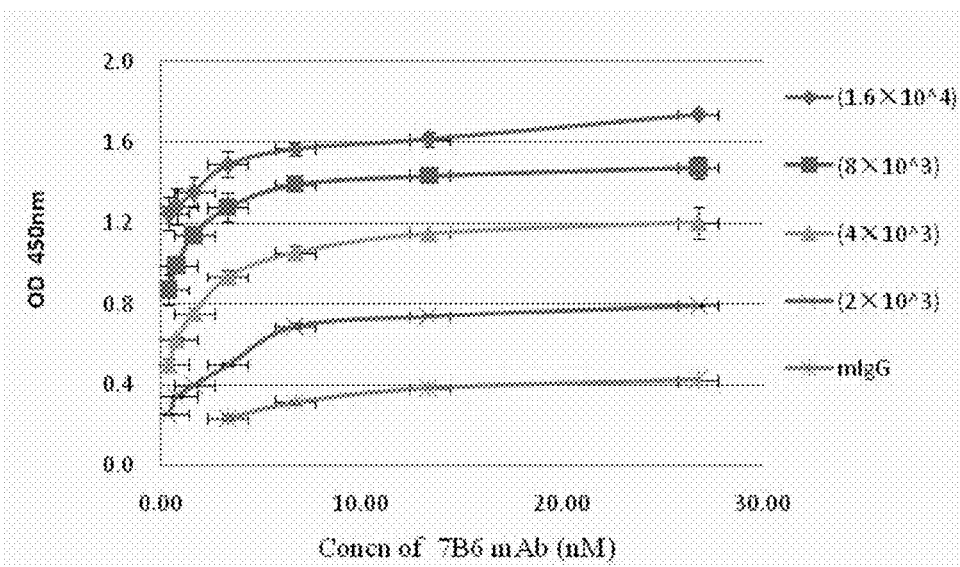
FIG. 5 shows the cell ELISA results of HPV16 E7 monoclonal antibody and cells. Experimental details are in Example 1, Section 2.6: the cell numbers of CaSki are $1.6×10^4$, $8×10^3$, $4×10^3$ and $2×10^3$. The incubating concentrations of 7B6 are dealt with double dilution then obtain 7 gradients and mIgG (4 µg/ml) is added into to conduct cell ELISA test as a negative control. Obtained values are plugged into $K_{aff}=(n-1)/2$ (n [Ab']−[Ab]) to get 6 values of K, then calculate for average value. Lastly the average cellar level affinity of 7B6 is 1.52 nM.

The monoclonal antibody cell binding affinity constant was determined according to the method of protein binding affinity. The HPV16 E7 expressed cervical cancer cell stains CaSki were transferred into 96-well culture plates with the amount of $1.6 \times 10^4$, $8 \times 10^3$, $4 \times 10^3$ and $2 \times 10^3$, then stayed for overnight at 37° C. 4% paraformaldehyde was used to fixe and 0.3% Triton X-100 TBS buffer liquid was added into cells, then cells were placed in room temperature for 15 min until the cytomembranes reached good permeability; TBS washing liquid was added to wash for 15 min then spin-dried; TBS buffer liquid with 1% $H_2O_2$ was used in order to inactive the endogenous peroxidase then spin-dried; TBS washing liquid was added to wash for 5 min then spin-dried; 10% FBS/TBS confining liquid was added and stayed overnight then spin-dried; mAb anti-HPV16E7 7B6 was doubling diluted from the concentration of 4 µg/ml and totally divided into 7 gradients, then mIgG (4 µg/ml) was added as negative control, incubated at 37° C. for 2 hours; The HPR second antibody was added as the second antibodies (Sigma A2554) (1:2000), 37° C., 1 hour, then developed with TMB and stopped with 2M $H_2SO_4$. Read at the position of OD450 nm. The obtained values were plot into $K_{aff}$=(n−1)/2(n[Ab']−[Ab]) to obtain the affinity constant. The results are shown in FIG. 5: The binding affinity of 7B6 and cervical cancer cell stains CaSki is 1.52 nM.

2.7 Detecting Endogenous HPV16 E7 of Monoclonal Antibody Combined Cancer Cells Through IP-WB $5×10^5$ literature reported HPV16 E7 positive cervical cancer cell stain CaSki cells and HPV negative cell stain C-33A (negative control) were added into cell lysis liquid containing 1 ml 1% Triton X-100, 1 mM EDTA, 50 mM NaCl, 0.1 (m/v) SDS, 1% sodium deoxycholate, 1 mM PMSF, 2 µg/ml aprotinin, 1 µg/ml leupeptin and 1 µg/ml pepstatin. Wherein all protease inhibitors should be added before using. Cells were placed on ice for lysis for 30 min, 12500 rpm, centrifugation for 10 min at 4° C., the obtained supernatant was the required protein extractives.

Figure 6:
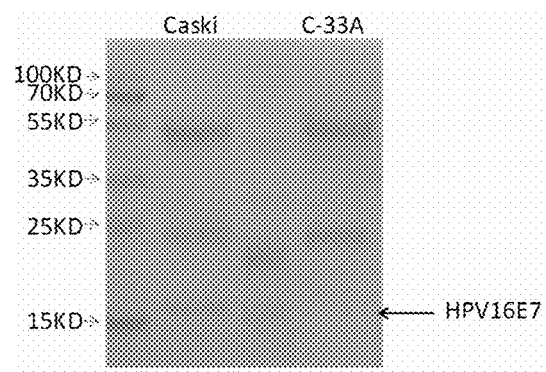
FIG. 6 shows the IP-WB results of HPV16 E7 monoclonal antibody 7B6 to HPV negative cell strains of C-33A (negative control) and HPV16 E7 monoclonal antibody 7B6 to internal HPV16 E7 of HPV positive CaSki cell strains. Experimental details are in Example 1, Section 2.7: internal HPV16 E7 proteins are detected at the area with molecular weight of 17 KDa. Among them, the light chains of antibody are detected at 25 KDa and the heavy chains are at 55 KDa.

2 µg monoclonal antibody was added into the cell lysis supernatant and incubated for 2 hours at 4° C., then 15 µl protein A/G beads was added and incubated overnight at 4° C. On the second day, beads were washed twice with cell lysis liquid without protease inhibitor, then 1×SDS buffer was added and immunoblotting assay was conducted. In immunoblotting assay, NC membrane and 100V voltage were used and then the membrane was transferred for 35 min. Then blocked for 2 hours with 5% skim milk powder, E7 monoclonal antibodies diluted with 5% skim milk powder was added. The concentration of antibody is 2 µg/ml, incubated overnight at 4° C., then TBS which contained 0.1% Tween was used to wash for four times and anti-mouse IgG (Fc specific)-peroxidase antibody (Sigma A2554) (1:1000) was added, incubated at room temperature for 1 h, DAB (Wuhan Boster SA2024), developed. The results are shown in FIG. 6, the arrow points at the position of 17 KDa molecular weight and antibodies can specifically identify the endogenous HPV16 E7 proteins of CaSki cells. The parallel control of C-33A cells are negative and further confirm the specificity of antibody binding endogenous proteins.

2.8 Detection of HPV E7 Expression in Cervical Cancer Cells Through Immunocytochemical Staining Monoclonal antibody 7B6 was used to conduct immunocytochemical staining for cervical cancer cell strain CaSki cells which expressed HPV16 E7 proteins, cervical cancer cell strain Hela cells which expressed HPV18 E7 proteins and cervical cancer cell strain C-33A cells which contain no HPV DNA. Specific experiment steps are as follows:

CaSki, Hela and C-33A cells were respectively grown onto the cover slips which were treated by poly-L-Lysine, then cells were cultured under the conditions of 37° C., 5% $CO_2$ for 24 h. 4% paraformaldehyde was used to fix and TBS buffer liquid which contains 0.3% Triton X-100 was added into cells, then cells were placed in room temperature for 15 min until the cytomembranes reached good permeability; TBS washing liquid was added to wash for 5 min then spin-dried; TBS buffer liquid with 1% $H_2O_2$ was used under room temperature for 5 min in order to inactive the endogenous peroxidase then spin-dried; TBS washing liquid was added to wash for 5 min then spin-dried; 10% FBS/TBS confining liquid was added and stayed overnight then spin-dried; mAb anti-HPV16E7 7B6 (2 µg/ml) was added and incubated at 37° C. for 2 h; The TBS/0.1% Tween washing liquid was added to wash for five times and 5 min for each then spin-dried; The second antibody of anti-mouse IgG (Fc specific)-peroxidase antibody (Sigma A2554) (1:1000) was added and incubated at 37° C. for 1 h; The TBS/0.1% Tween washing liquid was added to wash for five times and 5 min for each then spin-dried; Then DAB color-substrate solution was added (Beijing ZSGB-Bio Company ZLI-9017) and reacted under room temperature for 10 min. Then washed with distilled water to stop the reaction. the results were observed and recorded under microscope.

Figure 7:
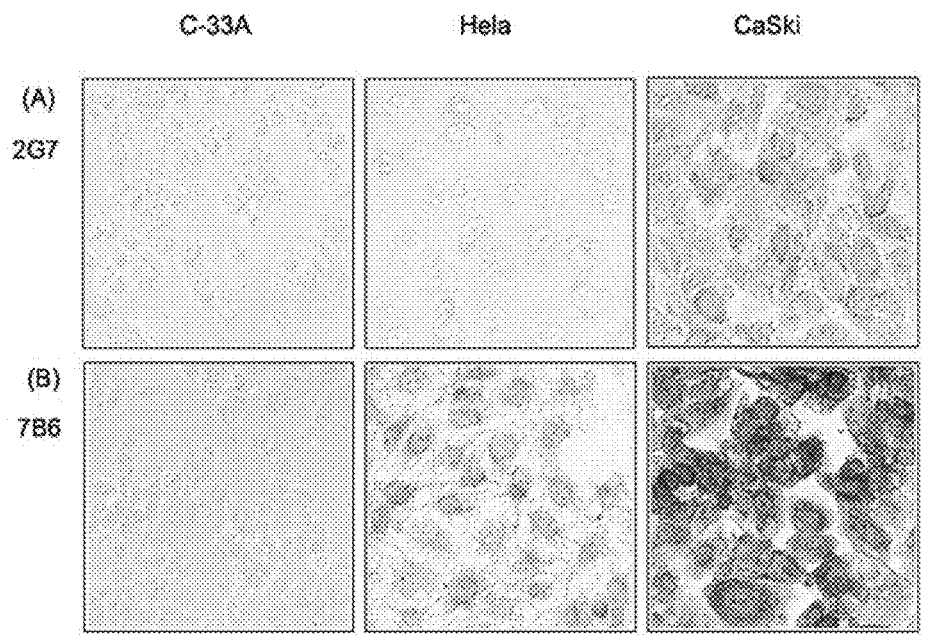
FIG. 7 shows the immunocytochemical staining results of HPV16 E7 monoclonal antibody. Experimental details are in Example 1, Section 2.8: A is the staining results of monoclonal antibody 2G7 to C-33A cells, Hela cells and CaSki cells respectively. B is the staining results of monoclonal antibody 7B6 to C-33A cells, Hela cells and CaSki cells respectively. 2G7 only has weak straining reaction to CaSki cells, while 7B6 has strong straining reaction to CaSki cells, weak reaction to Hela cells and no reaction to C-33A cells.
Figure 8:
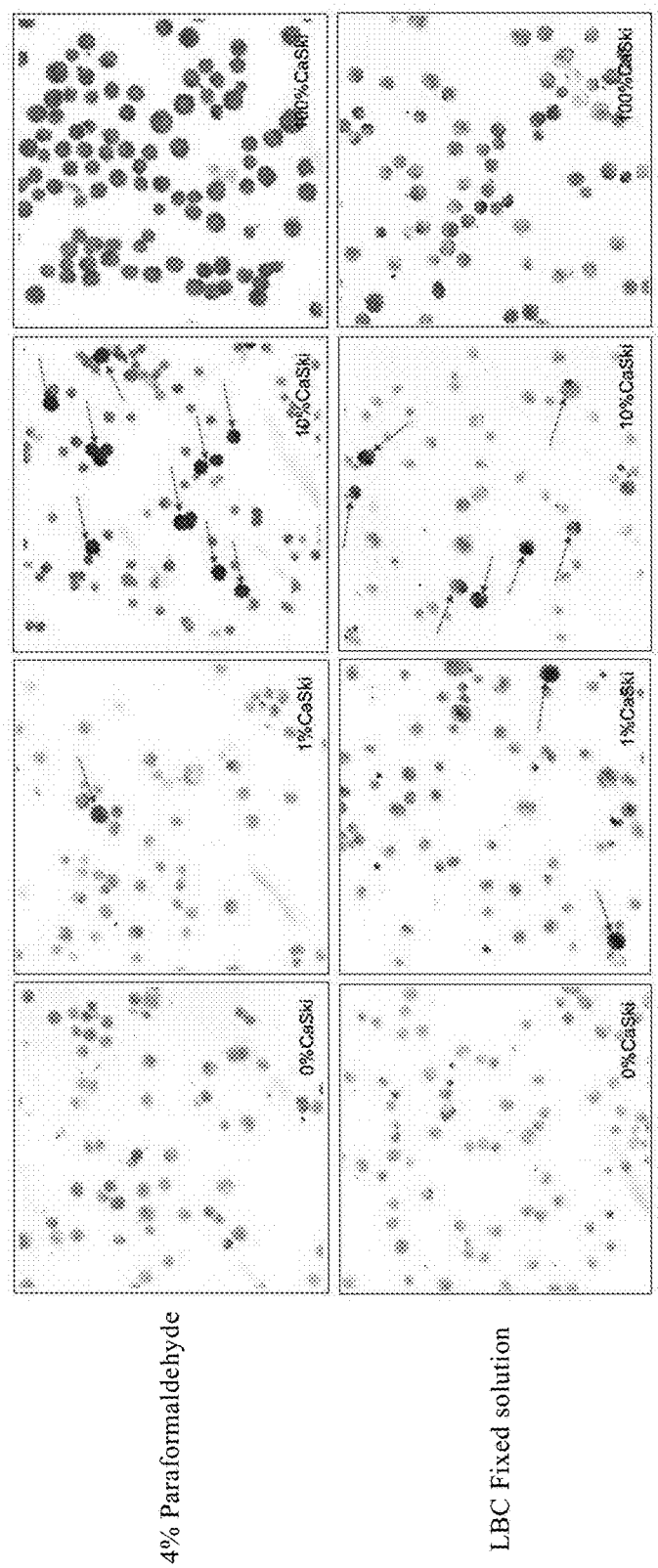
FIG. 8 shows the immunocytochemical staining results of cervical cancer C-33A cell strains and CaSki cells fixed with different stationary liquids strained by specific monoclonal antibody 7B6. Experimental details are in Example 2 of: no immunoreaction between C-33A cells and HPV16 E7 monoclonal antibodies 7B6; after two types of cells are mixed, CaSki cells with 1% or 10% of the total cells are strongly stained (red arrows) by HPV16 E7 monoclonal antibodies 7B6 and negative C-33A cells no staining. 100% Suspension fixed CaSki cells have strong immunoreaction with HPV16 E7 monoclonal antibody 7B6. 4% of paraformaldehyde and LBC stationary liquid have no effect to the specificities of HPV16 E7 monoclonal antibody 7B6 in ICC test.

The results are shown in FIG. 7. The results show that there is a weak immunochemical stain reaction between HPV16 E7 monoclonal antibody 2G7 and cervical cancer cell strain CaSki which expresses HPV16 E7 proteins. But there is no reaction between Hela cells expressed HPV18 E7 and cervical cancer cell strain C-33A which does not express HPV proteins (FIG. 7, A). However, after the incubation between monoclonal antibody 7B6 and CaSki cells, CaSki cells can be strongly stained, Hela cells can be weakly stained and no stain reaction with C-33A cells. The above results are consistent with the ELISA results which confirm the strong combination ability with 7B6 and cells' endogenous HPV16 E7 and slightly cross reaction between 7B6 and HPV18 E7, which means 7B6 can specifically identify endogenous HPV E7 proteins.

Example 2

Immunocytochemical Stain Detection for the Specificity of HPV16 E7 Monoclonal Antibody 7B6 in Suspension Fixed Cervical Cancer Cells Cervical cancer cell strain of CaSki cells expressed HPV16 E7 protein and cervical cancer cell strain of C-33A cells without HPV DNA were fixed by different stationary liquid then immunocytochemical staining experiment was performed with monoclonal antibody 7B6. Specific steps are as follows:

C-33A cells and CaSki cells were collected respectively, 4% paraformaldehyde or LBC stationary liquid was used to fix then the amount of cells was counted and the total amount should be around 10000. Among these 10000 cells, C-33A cells as negative control were mixed with CaSki cells at a specific ratio, the ratio of C-33A cells and CaSki cells could be 9:1, 99:1 or 999:1. The mixture was placed on the cover glasses treated with poly-L-Lysine for air dried, rendering the cell fixed on the cover glasses; t TBS washing liquid was used to wash for 5 min then spin-dried; TBS buffer liquid which contains 0.3% Triton X-100 was added into cells, then cells were placed under room temperature for 15 min until the cytomembranes reached good permeability; TBS washing liquid was added to wash for 5 min then spin-dried; TBS buffer liquid with 1% $H_2O_2$ was used under room temperature for 5 min in order to inactive the endogenous peroxidase then spin-dried; TBS washing liquid was added to wash for 5 min then spin-dried; 10% FBS/TBS confining liquid was added and stayed overnight then spin-dried; mAb anti-HPV16E7 7B6 (2 µg/ml) was added and incubated at 37° C. for 2 h; The TBS/0.1% Tween washing liquid was added to wash for five times and 5 min for each then spin-dried; The second antibody of anti-mouse IgG (Fc specific)-peroxidase antibody (Sigma A2554) (1:1000) was added and incubated at 37° C. for 1 h; The TBS/0.1% Tween washing liquid was added to wash for five times and 5 min for each then spin-dried; Then DAB color-substrate solution was added (Beijing ZSGB-Bio Company ZLI-9017) and reacted under room temperature for 10 min. Then washed with distilled water to stop the reaction. Hematoxylin staining solution (Beyotime Biotechnology C0107) was used to stain for 2 min then immersed into water to wash out redundant stain for about 10 min. Distilled water was used to wash again for several seconds then the results were observed and recorded under microscope.

The results show that there is only strong chemical staining reaction between HPV16 E7 specific monoclonal antibody 7B6 and cervical cancer cell strain CaSki only expressed HPV16 E7 protein but no chemical staining reaction with cervical cancer cell strain C-33A without HPV DNA. After CaSki cells and C-33A cells were mixed with the ratio of 1:9 or 1:99, 7B6 can specifically combine with CaSki cells but without combination with C-33A. that is, 7B6 can distinguish exactly neutral, negative cells and positive cells though the amount of positive cancer cells account for 1% or 10% of the total amount of cells. In addition, there is no effect on the judgment of positive or negative staining in ICC test using 4% paraformaldehyde or LBC stationary liquid to fix the cell.

Therefore, the results show that HPV16 E7 monoclonal antibody 7B6 can still specifically detect endogenous HPV16 E7 proteins in the tumor cells when cancer cells are pre-fixed by 4% paraformaldehyde or LBC stationary liquid for several days, that is, stationary liquid treatment will not make effects on staining results, such as staining weakened or background strengthened. Moreover, when the ratio of HPV16 E7 is reduced to 1%, 7B6 antibody can still accurately detect the target cells, indicating that the detection method has good specificity and sensitivity. Due to the widespread use of LBC detection techniques in clinical practice, the remaining cell samples can be provided for analysis of other HPV infections, whereas in this example, HPV E7-related cervical cancer cells can be accurately detected after several days of LBC fixation, therefore, this method can further be applied to develop the detection of related malignancies caused by persistent infection of HPV 16 E7 in the clinical practice.

Example 3

Immunohistochemical staining detection for the specificity of HPV16 E7 monoclonal antibody 7B6 in paraffin sections of SiHa nudemic tissue.

The SiHa was collected in logarithmic growth phase, $1 \times 10^6$ tumor cells (volume of 100 μl) were injected subcutaneously into the left inguinal of the mice to establish a tumor model. After the tumor was grown for a month, the tumor tissue was collected and fixed by neutral 10% formalin. And paraffin sections were prepared for immunohistochemical staining. The paraffin sections were immersed in xylene twice for 10 min each; then immersed in 100% ethanol, 95% ethanol, 90% ethanol, 80% ethanol, 70% ethanol and each for 5 min, then washed twice with PBS; The tissue sections were placed into boiled 0.01M sodium citrate buffer solution (pH 6.0) and heated for 15 min. Then cooled to room temperature, washed with PBS for three times and each for 5 min; in order to inactivate the endogenous peroxidase, PBS buffer solution containing 3% $H_2O_2$ was added and treated for 10 min at room temperature; then washed with PBS for three times and each for 5 min; PBS containing 10% sheep serum was added and blocked at room temperature for 15 min; then the confining liquid was abandoned and HPV16 E7 monoclonal antibody of 1H11 and 7B6 were added respectively, incubated overnight at the concentration of 30 μg/ml; Anti-Mouse-HRP (Dako) was added after sufficiently washed then incubated at room temperature for 30 min; developed with DBA for 5 min (observed under microscope) after sufficiently washed then washed with water for 5 min; hematoxylin was used for counterstaining for 2 min then washed with water; Dehydration stepwise then immersed in 70% ethanol, 80% ethanol, 95% ethanol, anhydrous ethanol and each for 5 min; Lastly, immersed in xylene twice and each for 10 min; After air drying, neutral gum was used for sealing then observed under microscope.

Figure 9:
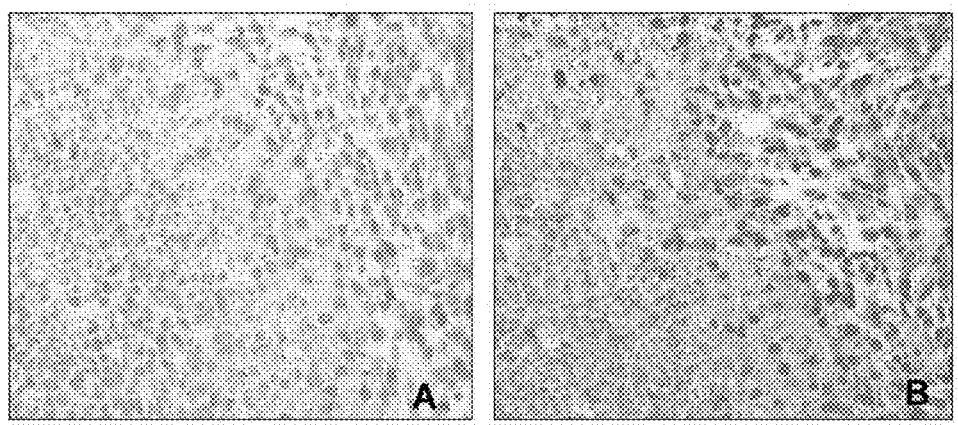
FIG. 9 shows the immunohistochemical staining results of HPV16 E7 monoclonal antibody in cervical cancer cell (SiHa) paraffin sections. Experimental details are in Example 3. (A) IHC staining results between monoclonal antibody 1H11 (30 µg/ml) and SiHa paraffin sections. (B) IHC staining results between monoclonal antibody 7B6 (30 µg/ml) and SiHa paraffin sections. The results show that monoclonal antibody 7B6 have strong staining reaction with SiHa paraffin sections, but monoclonal antibody 1H11 have no staining reaction with SiHa paraffin sections.

The results show that (FIG. 9): there is a strong immunohistochemical staining reaction between HPV16 E7 monoclonal antibody of 7B6 and paraffin sections of cervical cancer cell lines SiHa expressed HPV E7 proteins, while paraffin sections of 1H11 and SiHa cells were not stained.

Figure 10:
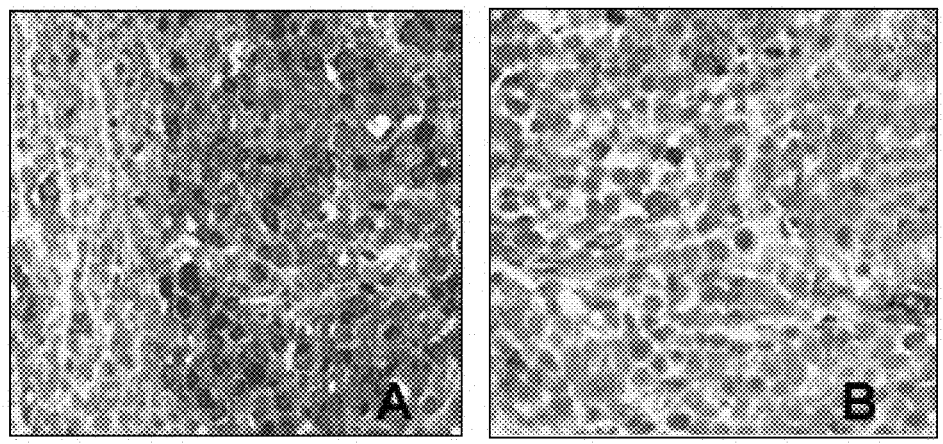
FIG. 10 shows the immunohistochemical staining results of HPV16 E7 monoclonal antibody in cervical cancer cell (SiHa) paraffin sections. Experimental details are in Example 3. (A) HPV16 E7 monoclonal antibody can strongly stain SiHa paraffin sections used alone. (B) Incubation of 7B6 and His-HPV16 E7 recombinant protein in advance reduces stain level to SiHa paraffin sections.

Further, in order to prove the specificity of combination between HPV16 E7 monoclonal antibody 7B6 and SiHa cell sections, His-HPV16E7 recombinant protein and 7B6 antibodies were pre-incubated to compete for the binding of 7B6 to the endogenous HPV E7 of SiHa cells. The concentration of 7B6 was 10 μg/ml and the concentration of His-HPV16E7 was 20 μg/ml. The results are shown in FIG. 10, the immunological staining reaction with the 7B6 antibody preliminarily adsorbed by the antigen-protein of His-HPV16E7 and the cervical cancer cell line SiHa were significantly decreased, indicating that the HPV16 E7 monoclonal antibody 7B6 is specifically binding to the HPV16E7 protein in tumor cells, indicating that the antibody can be used for immunohistochemical detection of HPV16 E7, for the application in scientific or clinical fields and for the further development of clinical cervical cancer detection.

All the documents cited herein are incorporated into the invention as reference, as if each of them is individually incorporated. Further, it would be appreciated that, in light of the above described teaching of the invention, the skilled in the art could make various changes or modifications to the invention, and these equivalents would still be in the scope of the invention defined by the appended claims of the application.

The invention claimed is:

1. A variable region of an anti-HPV E7 protein antibody, wherein the variable region is a heavy chain variable region comprising three complementary determining regions:
   CDR1 as shown in SEQ ID NO: 4;
   CDR2 as shown in SEQ ID NO: 6; and
   CDR3 as shown in SEQ ID NO: 8, or
the variable region is a light chain variable region comprising three complementary determining regions:
   CDR1' as shown in SEQ ID NO: 14;
   CDR2' as shown in SEQ ID NO: 16; and
   CDR3' as shown in SEQ ID NO: 18.

2. A recombinant protein having:
   (1) a heavy chain variable region comprising three complementary determining regions:
       CDR1 as shown in SEQ ID NO: 4;
       CDR2 as shown in SEQ ID NO: 6; and
       CDR3 as shown in SEQ ID NO: 8, and/or
   (2) a light chain variable region comprising three complementary determining regions:
       CDR1' as shown in SEQ ID NO: 14;
       CDR2' as shown in SEQ ID NO: 16; and
       CDR3' as shown in SEQ ID NO: 18.

3. The recombinant protein of claim 2 further having a tag sequence that assists in expression and/or purification.

4. The recombinant protein of claim 2 further comprising a coupling moiety including at least one selected from the group consisting of a detectable label, a drug, a toxin, a cytokine, a radionuclide, and an enzyme.

5. A method to detect a HPV E7 protein in a sample, wherein the method comprises steps of:
   (1) contacting a sample with an antibody wherein the antibody having:
       (a) a heavy chain variable region comprising three complementary determining regions:
           CDR1 as shown in SEQ ID NO: 4;
           CDR2 as shown in SEQ ID NO: 6; and
           CDR3 as shown in SEQ ID NO: 8; and
       (b) a light chain variable region comprising three complementary determining regions:
           CDR1' as shown in SEQ ID NO: 14;
           CDR2' as shown in SEQ ID NO: 16; and
           CDR3' as shown in SEQ ID NO: 18, and
   (2) detecting whether an antigen-antibody complex is formed, wherein the formation of the antigen-antibody complex indicates a presence of a HPV E7 protein in the sample.

6. A detection plate comprising a substrate and a test strip, wherein the test strip contains the recombinant protein of claim 2.

7. A kit comprising: (1) a first container comprising the recombinant protein of claim 2, optionally (2) a second container comprising a secondary antibody against the recombinant protein of claim 2, and optionally (3) a third container comprising reagents for cell lysis.

8. The recombinant protein of claim 2, wherein
   the heavy chain variable region has an amino acid sequence as shown in SEQ ID NO: 10; and/or
   the light chain variable region has an amino acid sequence as shown in SEQ ID NO: 20.

9. The recombinant protein of claim 2 having a heavy chain and/or a light chain, wherein the heavy chain has a heavy chain constant region and a heavy chain variable region comprising three complementary determining regions:
   CDR1 as shown in SEQ ID NO: 4;
   CDR2 as shown in SEQ ID NO: 6; and
   CDR3 as shown in SEQ ID NO: 8, and
the light chain has a light chain constant region and a light chain variable region comprising three complementary determining regions:
   CDR1' as shown in SEQ ID NO: 14;
   CDR2' as shown in SEQ ID NO: 16; and
   CDR3' as shown in SEQ ID NO: 18.

10. The recombinant protein of claim 2, wherein the recombinant protein is an antibody.

11. The recombinant protein of claim 10, wherein the antibody is an antibody specific anti-HPV16E7 protein and/or anti-HPV18E7 protein.

12. The recombinant protein of claim 10, wherein the antibody includes: a single chain antibody, a double chain antibody, a monoclonal antibody, a chimeric antibody including a human-mouse chimeric antibody, a murine antibody, or a humanized antibody.

13. The variable region of claim 1, wherein the heavy chain variable region has an amino acid sequence as shown in SEQ ID NO: 10.

14. The variable region of claim 1, wherein the light chain variable region has an amino acid sequence as shown in SEQ ID NO: 20.

15. The detection plate of claim 6, wherein the substrate includes a support chip.

* * * * *

SEQUENCE LISTING

```
<160> NUMBER OF SEQ ID NOS: 29

<210> SEQ ID NO 1
<211> LENGTH: 97
<212> TYPE: PRT
<213> ORGANISM: Human papilloma virus

<400> SEQUENCE: 1

His Gly Asp Thr Pro Thr Leu His Glu Tyr Met Leu Asp Leu Gln Pro
1               5                   10                  15

Glu Thr Thr Asp Leu Tyr Cys Tyr Glu Gln Leu Asn Asp Ser Ser Glu
            20                  25                  30
```

```
Glu Glu Asp Glu Ile Asp Gly Pro Ala Gly Gln Ala Glu Pro Asp Arg
            35                  40                  45

Ala His Tyr Asn Ile Val Thr Phe Cys Cys Lys Cys Asp Ser Thr Leu
 50                  55                  60

Arg Leu Cys Val Gln Ser Thr His Val Asp Ile Arg Thr Leu Glu Asp
 65                  70                  75                  80

Leu Leu Met Gly Thr Leu Gly Ile Val Cys Pro Ile Cys Ser Gln Lys
                 85                  90                  95

Pro

<210> SEQ ID NO 2
<211> LENGTH: 105
<212> TYPE: PRT
<213> ORGANISM: Human papilloma virus

<400> SEQUENCE: 2

Met His Gly Pro Lys Ala Thr Leu Gln Asp Ile Val Leu His Leu Glu
 1               5                  10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
 50                  55                  60

Cys Cys Lys Cys Glu Ala Arg Ile Glu Leu Val Val Glu Ser Ser Ala
 65                  70                  75                  80

Asp Asp Leu Arg Ala Phe Gln Gln Leu Phe Leu Asn Thr Leu Ser Phe
                 85                  90                  95

Val Cys Pro Trp Cys Ala Ser Gln Gln
                100                 105

<210> SEQ ID NO 3
<211> LENGTH: 24
<212> TYPE: DNA
<213> ORGANISM: Artificial sequence
<220> FEATURE:
<223> OTHER INFORMATION: Antibody CDR

<400> SEQUENCE: 3
ggttactcat tcactggctc cacc                                           24

<210> SEQ ID NO 4
<211> LENGTH: 8
<212> TYPE: PRT
<213> ORGANISM: Artificial sequence
<220> FEATURE:
<223> OTHER INFORMATION: Antibody CDR

<400> SEQUENCE: 4

Gly Tyr Ser Phe Thr Gly Ser Thr
 1               5

<210> SEQ ID NO 5
<211> LENGTH: 24
<212> TYPE: DNA
<213> ORGANISM: Artificial sequence
<220> FEATURE:
<223> OTHER INFORMATION: Antibody CDR

<400> SEQUENCE: 5
attgatcctt acaatggtgt tatt                                           24
```

<210> SEQ ID NO 6
<211> LENGTH: 8
<212> TYPE: PRT
<213> ORGANISM: Artificial sequence
<220> FEATURE:
<223> OTHER INFORMATION: Antibody CDR

<400> SEQUENCE: 6

Ile Asp Pro Tyr Asn Gly Val Ile
1               5

<210> SEQ ID NO 7
<211> LENGTH: 18
<212> TYPE: DNA
<213> ORGANISM: Artificial sequence
<220> FEATURE:
<223> OTHER INFORMATION: Antibody CDR

<400> SEQUENCE: 7
gcaagaaagt tgcgctac                                              18

<210> SEQ ID NO 8
<211> LENGTH: 6
<212> TYPE: PRT
<213> ORGANISM: Artificial sequence
<220> FEATURE:
<223> OTHER INFORMATION: Antibody CDR

<400> SEQUENCE: 8

Ala Arg Lys Leu Arg Tyr
1               5

<210> SEQ ID NO 9
<211> LENGTH: 339
<212> TYPE: DNA
<213> ORGANISM: Artificial sequence
<220> FEATURE:
<223> OTHER INFORMATION: Heavy chain variable region of antibody

<400> SEQUENCE: 9
aggtcaagct gcaggagtct ggacctgagc tggtgaagcc tggagcttca atgaagatat      60
cctgcaaggc ttctggttac tcattcactg gctccaccat gaactgggtg aagcagagcc     120
atggaaagaa ccttgagtgg attggactta ttgatcctta caatggtgtt attaggtaca     180
accagaagtt caagggcagg gccacattaa ctatagacaa gtcatccagc acagcctaca     240
tggagctcct cagtctgaca tctgatgact ctgcagtcta ttactgtgca agaaagttgc     300
gctactgggg ccaaggcacc actctcacag tatcctcag                            339

<210> SEQ ID NO 10
<211> LENGTH: 112
<212> TYPE: PRT
<213> ORGANISM: Artificial sequence
<220> FEATURE:
<223> OTHER INFORMATION: Heavy chain variable region of antibody

<400> SEQUENCE: 10

Val Lys Leu Gln Glu Ser Gly Pro Glu Leu Val Lys Pro Gly Ala Ser
1               5                   10                  15

Met Lys Ile Ser Cys Lys Ala Ser Gly Tyr Ser Phe Thr Gly Ser Thr
            20                  25                  30

Met Asn Trp Val Lys Gln Ser His Gly Lys Asn Leu Glu Trp Ile Gly
        35                  40                  45

Leu Ile Asp Pro Tyr Asn Gly Val Ile Arg Tyr Asn Gln Lys Phe Lys
    50                  55                  60

Gly Arg Ala Thr Leu Thr Ile Asp Lys Ser Ser Ser Thr Ala Tyr Met
65                  70                  75                  80

Glu Leu Leu Ser Leu Thr Ser Asp Asp Ser Ala Val Tyr Tyr Cys Ala
                85                  90                  95

Arg Lys Leu Arg Tyr Trp Gly Gln Gly Thr Thr Leu Thr Val Ser Ser
            100                 105                 110

<210> SEQ ID NO 11
<211> LENGTH: 24
<212> TYPE: PRT
<213> ORGANISM: Artificial sequence
<220> FEATURE:
<223> OTHER INFORMATION: Antibody FR

<400> SEQUENCE: 11

Val Lys Leu Gln Glu Ser Gly Pro Glu Leu Val Lys Pro Gly Ala Ser
1               5                   10                  15

Met Lys Ile Ser Cys Lys Ala Ser
            20

<210> SEQ ID NO 12
<211> LENGTH: 17
<212> TYPE: PRT
<213> ORGANISM: Artificial sequence
<220> FEATURE:
<223> OTHER INFORMATION: Antibody FR

<400> SEQUENCE: 12

Met Asn Trp Val Lys Gln Ser His Gly Lys Asn Leu Glu Trp Ile Gly
1               5                   10                  15

Leu

<210> SEQ ID NO 13
<211> LENGTH: 36
<212> TYPE: DNA
<213> ORGANISM: Artificial sequence
<220> FEATURE:
<223> OTHER INFORMATION: Antibody CDR

<400> SEQUENCE: 13
cagagtctgt taaacagtgg aaatcaaagg aactac                              36

<210> SEQ ID NO 14
<211> LENGTH: 12
<212> TYPE: PRT
<213> ORGANISM: Artificial sequence
<220> FEATURE:
<223> OTHER INFORMATION: Antibody CDR

<400> SEQUENCE: 14

Gln Ser Leu Leu Asn Ser Gly Asn Gln Arg Asn Tyr
1               5                   10

<210> SEQ ID NO 15
<211> LENGTH: 9
<212> TYPE: DNA
<213> ORGANISM: Artificial sequence
<220> FEATURE:
<223> OTHER INFORMATION: Antibody CDR

<400> SEQUENCE: 15 ggggcatcc                                                                  9

<210> SEQ ID NO 16
<211> LENGTH: 3
<212> TYPE: PRT
<213> ORGANISM: Artificial sequence
<220> FEATURE:
<223> OTHER INFORMATION: Antibody CDR

<400> SEQUENCE: 16

Gly Ala Ser
1

<210> SEQ ID NO 17
<211> LENGTH: 27
<212> TYPE: DNA
<213> ORGANISM: Artificial sequence
<220> FEATURE:
<223> OTHER INFORMATION: Antibody CDR

<400> SEQUENCE: 17
cagaatgatc ttagttatcc tctcacg                                              27

<210> SEQ ID NO 18
<211> LENGTH: 9
<212> TYPE: PRT
<213> ORGANISM: Artificial sequence
<220> FEATURE:
<223> OTHER INFORMATION: Antibody CDR

<400> SEQUENCE: 18

Gln Asn Asp Leu Ser Tyr Pro Leu Thr
1               5

<210> SEQ ID NO 19
<211> LENGTH: 333
<212> TYPE: DNA
<213> ORGANISM: Artificial sequence
<220> FEATURE:
<223> OTHER INFORMATION: Light chain variable region of antibody

<400> SEQUENCE: 19
gtgctacaca gtctccatcc tccctgaatg tgtcaccagg agagaaggtc actatgagct          60
gcaagtccag tcagagtctg ttaaacagtg gaaatcaaag gaactacttg gcctggtacc         120
agcagaaacc aggacagcct cctaaactgt tgatctacgg ggcatccact agggagtctg         180
gggtccctga tcgcttcacc ggcagtggat ctggaaccga tttcactctt accatcagca         240
gtgtgcaggc tgaagacctg gcagtttatt actgtcagaa tgatcttagt tatcctctca         300
cgttcggtgc tgggaccaag ctggagctga aac                                      333

<210> SEQ ID NO 20
<211> LENGTH: 110
<212> TYPE: PRT
<213> ORGANISM: Artificial sequence
<220> FEATURE:
<223> OTHER INFORMATION: Light chain variable region of antibody

<400> SEQUENCE: 20

Ala Thr Gln Ser Pro Ser Ser Leu Asn Val Ser Pro Gly Glu Lys Val
1               5                   10                  15

Thr Met Ser Cys Lys Ser Ser Gln Ser Leu Leu Asn Ser Gly Asn Gln
            20                  25                  30

Arg Asn Tyr Leu Ala Trp Tyr Gln Gln Lys Pro Gly Gln Pro Pro Lys

```
                35                  40                  45
Leu Leu Ile Tyr Gly Ala Ser Thr Arg Glu Ser Gly Val Pro Asp Arg
 50                  55                  60

Phe Thr Gly Ser Gly Ser Gly Thr Asp Phe Thr Leu Thr Ile Ser Ser
 65                  70                  75                  80

Val Gln Ala Glu Asp Leu Ala Val Tyr Tyr Cys Gln Asn Asp Leu Ser
                 85                  90                  95

Tyr Pro Leu Thr Phe Gly Ala Gly Thr Lys Leu Glu Leu Lys
            100                 105                 110

<210> SEQ ID NO 21
<211> LENGTH: 38
<212> TYPE: PRT
<213> ORGANISM: Artificial sequence
<220> FEATURE:
<223> OTHER INFORMATION: Antibody FR

<400> SEQUENCE: 21

Arg Tyr Asn Gln Lys Phe Lys Gly Arg Ala Thr Leu Thr Ile Asp Lys
 1               5                  10                  15

Ser Ser Ser Thr Ala Tyr Met Glu Leu Leu Ser Leu Thr Ser Asp Asp
                20                  25                  30

Ser Ala Val Tyr Tyr Cys
         35

<210> SEQ ID NO 22
<211> LENGTH: 11
<212> TYPE: PRT
<213> ORGANISM: Artificial sequence
<220> FEATURE:
<223> OTHER INFORMATION: Antibody FR

<400> SEQUENCE: 22

Trp Gly Gln Gly Thr Thr Leu Thr Val Ser Ser
 1               5                  10

<210> SEQ ID NO 23
<211> LENGTH: 21
<212> TYPE: PRT
<213> ORGANISM: Human papilloma virus

<400> SEQUENCE: 23

Lys Cys Asp Ser Thr Leu Arg Leu Cys Val Gln Ser Thr His Val Asp
 1               5                  10                  15

Ile Arg Thr Leu Glu
            20

<210> SEQ ID NO 24
<211> LENGTH: 24
<212> TYPE: PRT
<213> ORGANISM: Human papilloma virus

<400> SEQUENCE: 24

Leu Asn Asp Ser Ser Glu Glu Glu Asp Glu Ile Asp Gly Pro Ala Gly
 1               5                  10                  15

Gln Ala Glu Pro Asp Arg Ala His
            20

<210> SEQ ID NO 25
<211> LENGTH: 55
<212> TYPE: PRT
<213> ORGANISM: Human papilloma virus
```

<400> SEQUENCE: 25

Asp Glu Ile Asp Gly Pro Ala Gly Gln Ala Glu Pro Asp Arg Ala His
1               5                   10                  15

Tyr Asn Ile Val Thr Phe Cys Cys Lys Cys Asp Ser Thr Leu Arg Leu
                20                  25                  30

Cys Val Gln Ser Thr His Val Asp Ile Arg Thr Leu Glu Asp Leu Leu
                35                  40                  45

Met Gly Thr Leu Gly Ile Val
    50                  55

<210> SEQ ID NO 26
<211> LENGTH: 26
<212> TYPE: PRT
<213> ORGANISM: Artificial sequence
<220> FEATURE:
<223> OTHER INFORMATION: Antibody FR

<400> SEQUENCE: 26

Glu Leu Val Leu Thr Gln Ser Pro Ser Ser Leu Asn Val Ser Pro Gly
1               5                   10                  15

Glu Lys Val Thr Met Ser Cys Lys Ser Ser
                20                  25

<210> SEQ ID NO 27
<211> LENGTH: 17
<212> TYPE: PRT
<213> ORGANISM: Artificial sequence
<220> FEATURE:
<223> OTHER INFORMATION: Antibody FR

<400> SEQUENCE: 27

Leu Ala Trp Tyr Gln Gln Lys Pro Gly Gln Pro Pro Lys Leu Leu Ile
1               5                   10                  15

Tyr

<210> SEQ ID NO 28
<211> LENGTH: 36
<212> TYPE: PRT
<213> ORGANISM: Artificial sequence
<220> FEATURE:
<223> OTHER INFORMATION: Antibody FR

<400> SEQUENCE: 28

Thr Arg Glu Ser Gly Val Pro Asp Arg Phe Thr Gly Ser Gly Ser Gly
1               5                   10                  15

Thr Asp Phe Thr Leu Thr Ile Ser Ser Val Gln Ala Glu Asp Leu Ala
                20                  25                  30

Val Tyr Tyr Cys
            35

<210> SEQ ID NO 29
<211> LENGTH: 10
<212> TYPE: PRT
<213> ORGANISM: Artificial sequence
<220> FEATURE:
<223> OTHER INFORMATION: Antibody FR

<400> SEQUENCE: 29

Phe Gly Ala Gly Thr Lys Leu Glu Leu Lys
1               5                   10